United States Patent
Atienza et al.

(10) Patent No.: US 10,927,134 B2
(45) Date of Patent: Feb. 23, 2021

(54) BRIDGED PHENOLATE TRANSITION METAL COMPLEXES, PRODUCTION, AND USES THEREOF

(71) Applicant: ExxonMobil Chemical Patents Inc., Baytown, TX (US)

(72) Inventors: Crisita Carmen H. Atienza, Houston, TX (US); David A. Cano, Houston, TX (US); Catherine A. Faler, Houston, TX (US); Margaret T. Whalley, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 16/550,892

(22) Filed: Aug. 26, 2019

(65) Prior Publication Data
US 2020/0071345 A1 Mar. 5, 2020

Related U.S. Application Data

(60) Provisional application No. 62/723,809, filed on Aug. 28, 2018.

(51) Int. Cl.
| | | |
|---|---|---|
| *C08F 4/64* | (2006.01) | |
| *C08F 4/76* | (2006.01) | |
| *C07F 7/00* | (2006.01) | |
| *C07D 209/86* | (2006.01) | |
| *C08F 10/06* | (2006.01) | |
| *C08F 10/14* | (2006.01) | |
| *C08F 10/02* | (2006.01) | |

(52) U.S. Cl.
CPC .............. *C07F 7/00* (2013.01); *C07D 209/86* (2013.01); *C08F 10/02* (2013.01); *C08F 10/06* (2013.01); *C08F 10/14* (2013.01); *C08F 4/64* (2013.01); *C08F 4/64189* (2013.01); *C08F 4/64193* (2013.01)

(58) Field of Classification Search
CPC .............. C08F 4/64189; C08F 4/64193; C08F 4/60189; C08F 4/60193; C08F 4/62189; C08F 4/62193; C07F 17/00
See application file for complete search history.

(56) References Cited

U.S. PATENT DOCUMENTS

| | | | |
|---|---|---|---|
| 8,071,701 B2 | 12/2011 | Klosin et al. | |
| 8,937,137 B2 * | 1/2015 | Holtcamp | C08F 110/06 526/172 |
| 8,952,114 B2 * | 2/2015 | Giesbrecht | C08F 10/00 526/161 |
| 8,957,171 B2 * | 2/2015 | Giesbrecht | C08F 210/16 526/161 |
| 9,292,589 B2 * | 3/2016 | Palmert | G06F 16/9535 |
| 9,365,661 B2 * | 6/2016 | Giesbrecht | C08F 10/00 |
| 9,382,349 B2 * | 7/2016 | Harrington | C08F 4/64189 |
| 9,493,587 B2 * | 11/2016 | Kol | C07C 215/50 |
| 9,975,973 B2 * | 5/2018 | Atienza | C08F 210/16 |
| 9,994,657 B2 * | 6/2018 | Atienza | C08F 4/64189 |
| 10,000,593 B2 * | 6/2018 | Ye | C08F 210/16 |
| 10,221,260 B2 * | 3/2019 | Atienza | C08F 10/06 |
| 2018/0030167 A1 | 2/2018 | Atienza et al. | |

FOREIGN PATENT DOCUMENTS

| | | |
|---|---|---|
| CN | 105061493 | 1/2018 |
| WO | 2002/036638 | 5/2002 |
| WO | 2003/091262 | 11/2003 |
| WO | 2007/075299 | 7/2007 |
| WO | 2014/070502 | 5/2014 |
| WO | 2015/088819 | 6/2015 |
| WO | 2016/094866 | 6/2016 |
| WO | 2016/094870 | 6/2016 |
| WO | 2016/153682 | 9/2016 |
| WO | 2017/058391 | 4/2017 |
| WO | 2017/058392 | 4/2017 |

OTHER PUBLICATIONS

Tshuva ,E. Y. et al. (2000) "Isospecific Living Polymerization of 1-Hexane by a Readily Available Nonmetallocene C2-Symmetrical Zirconium Catalyst", Jour. of Amer. Chem. Soc., v.122(43), pp. 10706-10707.

* cited by examiner

Primary Examiner — Rip A Lee

(57) ABSTRACT

The present disclosure provides transition metal catalysts and the respective bridged phenolate ligands contained on the catalyst, as well as, catalyst systems and polymerization processes for producing polyolefins. The catalysts and the catalyst systems provide catalytic activity values of greater than 100 kg/mmol-hr, such as greater than 400 kg/mmol-hr or greater than 500 kg/mmol-hr.

44 Claims, No Drawings

BRIDGED PHENOLATE TRANSITION METAL COMPLEXES, PRODUCTION, AND USES THEREOF

CROSS-REFERENCE TO RELATED APPLICATIONS

This application claims priority to and the benefit of U.S. Ser. No. 62/723,809, filed Aug. 28, 2018 and is incorporated by reference in its entirety.

FIELD

The present disclosure provides catalysts containing bridged phenolate transition metal complexes, production, and uses thereof.

BACKGROUND

Polyolefins are widely used commercially because of their robust physical properties. For example, various types of polyethylenes, including high density, low density, and linear low density polyethylenes, are some of the most commercially useful. Polyolefins are typically prepared with a catalyst that polymerizes olefin monomers. Therefore, there is interest in finding new catalysts and catalyst systems that provide polymers having improved properties.

Low density polyethylene is generally prepared at high pressure using free radical initiators, or in gas phase processes using Ziegler-Natta or vanadium catalysts. Low density polyethylene typically has a density in the range of 0.916 to 0.940 g/cm$^3$. Typical low density polyethylene produced using free radical initiators is known in the industry as "LDPE". LDPE is also known as "branched" or "heterogeneously branched" polyethylene because of the relatively large number of long chain branches extending from the main polymer backbone. Polyethylene in the same density range, e.g., 0.916 to 0.940 g/cm$^3$, which is linear and does not contain long chain branching, is known as "linear low density polyethylene" ("LLDPE") and is typically produced by conventional Ziegler-Natta catalysts or with metallocene catalysts. "Linear" means that the polyethylene has few, if any, long chain branches, typically referred to as a g'$_{vis}$ value of 0.97 or above, such as 0.98 or above. Polyethylenes having still greater density are the high density polyethylenes ("HDPEs"), e.g., polyethylenes having densities greater than 0.940 g/cm$^3$, and are generally prepared with Ziegler-Natta catalysts or chrome catalysts. Very low density polyethylenes ("VLDPEs") can be produced by a number of different processes yielding polyethylenes having a density less than 0.916 g/cm$^3$, typically 0.890 to 0.915 g/cm$^3$ or 0.900 to 0.915 g/cm$^3$.

Polyolefins, such as polyethylene, which have high molecular weight, generally have desirable mechanical properties over their lower molecular weight counterparts. However, high molecular weight polyolefins can be difficult to process and can be costly to produce. As used herein, "high molecular weight" is defined as a number average molecular weight (Mn) value of 100,000 or more. "Low molecular weight" is defined as an Mn value of less than 100,000.

Nonetheless, polyolefin compositions formed by catalysts capable of forming high molecular weight polyolefins typically also have a broad molecular weight distribution, as indicated by high polydispersity indices, and/or the polyolefins are of such high molecular weight (e.g., Mn of 1,500,000) as to have processing difficulty due to hardness.

Furthermore, catalysts capable of forming high molecular weight polyolefins typically have low polymer productivity.

There is a need for catalysts with a relatively high activity in order to form polyolefins, such as polyethylene, with high molecular weight and narrow molecular weight distribution and maintaining or increasing polyolefin productivity.

SUMMARY

The present disclosure provides transition metal catalysts and the respective bridged phenolate ligands contained on the catalyst, as well as, catalyst systems and polymerization processes. The bridged phenolate ligands are asymmetrical due in part to two linking diyl groups that are different lengths.

In one or more embodiments, the ligand is represented by Formula (I) and the transition metal complex is represented by Formula (II):

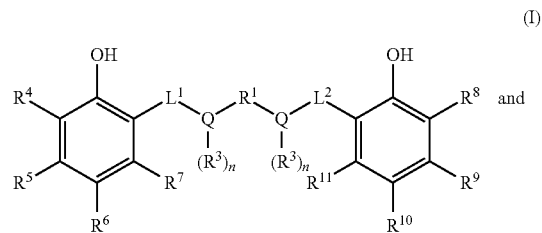

(I)

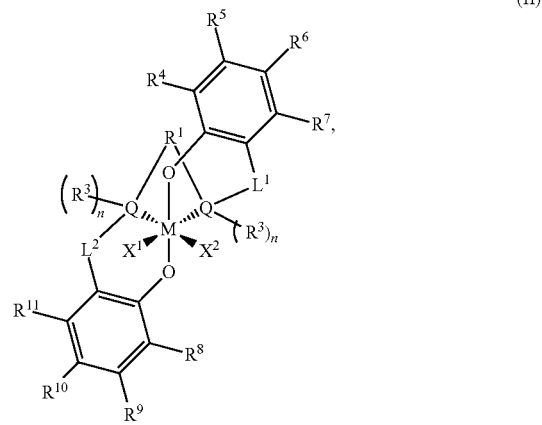

(II)

wherein:

M is a Group 4 transition metal;

each Q is independently a Group 15 atom or a Group 16 atom;

each n is independently 0 or 1, wherein n is 0 if Q is a Group 16 atom or n is 1 if Q is a Group 15 atom;

L$^1$ is

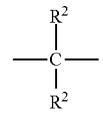

and is not part of an aromatic ring;
L² is

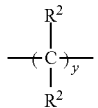

and is not part of an aromatic ring, wherein y is an integer of 2, 3, 4, 5, 6, 7, 8, 9, or 10;

- each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;
- $R^1$ is a substituted or unsubstituted linear, branched, cyclic, polycyclic, heterocyclic, or aromatic $C_1$-$C_{18}$ diyl;
- each $R^2$ is independently a hydrogen, a halogen, a substituted or unsubstituted $C_1$-$C_{40}$ hydrocarbyl, or a heteroatom-containing group; or two or more adjacent $R^2$ groups are joined together to form a $C_4$-$C_{62}$ cyclic, polycyclic, or heterocyclic group that is not aromatic;
- each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and
- each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

In some embodiments, the present disclosure provides a catalyst system that includes a catalyst compound represented by Formula (II), one or more activators, and an optional catalyst support.

In other embodiments, the present disclosure provides a polymerization process that includes contacting one or more olefin monomers with a catalyst system of the present disclosure and recovering an olefin polymer.

DETAILED DESCRIPTION

The present disclosure provides catalysts containing bridged phenolate transition metal complexes, production, and uses thereof. Catalysts of the present disclosure are transition metal complexes that have a bridged phenolate ligand located on the transition metal and provide catalytic activity values of greater than 100 kg/mmol-hr, such as greater than 400 kg/mmol-hr or greater than 500 kg/mmol-hr. Without being bound by theory, it is believed that the relatively high catalytic activity is at least in part due to the asymmetry of the bridged phenolate ligands caused by two linking diyl groups differing in the number of bridging atoms.

The specification describes catalysts that can be transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bonds, electron donation coordination, and/or intermediate bonds. The transition metal complexes are generally subjected to activation to perform their polymerization or oligomerization function using an activator which is believed to create a cation as a result of the removal of an anionic group, often referred to as a leaving group, from the transition metal.

For the purposes of the present disclosure, the numbering scheme for the Periodic Table Groups is used as described in *Chemical and Engineering News*, v. 63(5), pg. 27 (1985). Therefore, a "Group 4 metal" is an element from Group 4 of the Periodic Table, e.g., Hf, Ti, or Zr.

The term "substituted" means that at least one hydrogen atom has been replaced with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

The terms "hydrocarbyl radical," "hydrocarbyl," "hydrocarbyl group," "alkyl radical," and "alkyl" are used interchangeably throughout this disclosure. Likewise, the terms "group", "radical", and "substituent" are also used interchangeably in this disclosure. For purposes of this disclosure, "hydrocarbyl radical" is defined to be $C_1$-$C_{100}$ radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted hydrocarbyl radicals are radicals in which at least one hydrogen atom of the hydrocarbyl radical has been substituted with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, and the like, or where at least one heteroatom has been inserted within a hydrocarbyl ring.

The term "diyl," "diyl group," and "diyl radical" are used interchangeably throughout this disclosure. For purposes of this disclosure, "diyl" is defined to be $C_1$-$C_{40}$ divalent groups, that may be substituted or unsubstituted linear, branched, cyclic, polycyclic, heterocyclic, or aromatic. In examples throughout this disclosure, diyls can be or include, but are not limited to, $C_1$-$C_{40}$ diyls, $C_1$-$C_{25}$ diyls, $C_1$-$C_{18}$ diyls, $C_1$-$C_{12}$ diyls, $C_1$-$C_{10}$ diyls, and $C_1$-$C_5$ diyls. Examples of a $C_1$-$C_5$ diyl can be or include, but are not limited to, methanediyl (—CH$_2$—), ethanediyl (—CH$_2$CH$_2$—), propanediyl (—CH$_2$CH$_2$CH$_2$—), butanediyl (—CH$_2$(CH$_2$)$_2$CH$_2$—), and pentanediyl (—CH$_2$(CH$_2$)$_3$CH$_2$—), isomers thereof, halide-substituted analogues thereof, or other substituted analogues thereof.

The term "alkenyl" means a straight-chain, branched-chain, or cyclic hydrocarbon radical having one or more carbon-carbon double bonds. These alkenyl radicals may be substituted. Examples of suitable alkenyl radicals include, but are not limited to, ethenyl, propenyl, allyl, 1,4-butadienyl cyclopropenyl, cyclobutenyl, cyclopentenyl, cyclohexenyl, cyclooctenyl and the like including their substituted analogues.

The term "arylalkenyl" means an aryl group where a hydrogen has been replaced with an alkenyl or substituted alkenyl group. For example, styryl indenyl is an indene substituted with an arylalkenyl group (a styrene group).

The term "alkoxy" or "alkoxide" means an alkyl ether or aryl ether radical wherein the term alkyl is as defined above. Examples of suitable alkyl ether radicals include, but are not limited to, methoxy, ethoxy, n-propoxy, iso-propoxy, n-butoxy, iso-butoxy, sec-butoxy, tert-butoxy, phenoxy, and the like.

The term "aryl" or "aryl group" means a carbon-containing aromatic ring and the substituted variants thereof, including but not limited to, phenyl, 2-methyl-phenyl, xylyl, 4-bromo-xylyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

The term "arylalkyl" means an aryl group where a hydrogen has been replaced with an alkyl or substituted alkyl group. For example, 3,5'-di-tert-butyl-phenyl indenyl is an indene substituted with an arylalkyl group.

The term "alkylaryl" means an alkyl group where a hydrogen has been replaced with an aryl or substituted aryl group. For example, ethylbenzyl indenyl is an indene substituted with an ethyl group bound to a benzyl group.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "ring atom" means an atom that is part of a cyclic ring structure. By this definition, a benzyl group has six ring atoms and tetrahydrofuran has 5 ring atoms. A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system. Catalysts of the presented disclosure represented by Formula (II) are intended to embrace ionic forms in addition to the neutral forms of the compounds.

"Complex" as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Noncoordinating anion (NCA) means an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. The term non-coordinating anion activator includes neutral activators, ionic activators, and Lewis acid activators.

"Catalyst productivity" is a measure of how many grams of polymer (P) are produced using a polymerization catalyst containing W g of catalyst (cat), over a period of time of T hours; and may be expressed by the following formula: $P/(T \times W)$ and expressed in units of $gPgcat^{-1} hr^{-1}$. "Conversion" is the amount of monomer that is converted to polymer product, and is reported as mol % and is calculated based on the polymer yield and the amount of monomer fed into the reactor. "Catalyst activity" is a measure of the level of activity of the catalyst and is reported as the mass of product polymer (P) produced per mole of catalyst (cat) used (kgP/molcat).

For purposes herein an "olefin," alternatively referred to as "alkene," is a linear, branched, or cyclic compound containing carbon and hydrogen having at least one double bond. For purposes of this specification and the claims appended thereto, when a polymer or copolymer is referred to as containing an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and the derived units are present at 35 wt % to 55 wt %, based upon the weight of the copolymer.

For purposes herein a "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such an Mn of less than 25,000 g/mol, or less than 2,500 g/mol, or a low number of mer units, such as 75 mer units or less or 50 mer units or less. An "ethylene polymer" or "ethylene copolymer" is a polymer or copolymer containing at least 50 mol % ethylene derived units, a "propylene polymer" or "propylene copolymer" is a polymer or copolymer containing at least 50 mol % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol.

The term "continuous" means a system that operates without interruption or cessation for a period of time, where reactants are continually fed into a reaction zone and products are continually or regularly withdrawn without stopping the reaction in the reaction zone. For example, a continuous process to produce a polymer would be one where the reactants are continually introduced into one or more reactors and polymer product is continually withdrawn.

A "solution polymerization" means a polymerization process in which the polymerization is conducted in a liquid polymerization medium, such as an inert solvent or monomer(s) or their blends. A solution polymerization is typically homogeneous. A homogeneous polymerization is one where the polymer product is dissolved in the polymerization medium. Such systems are not turbids as described in Oliveira, J. V. et al. (2000) "High-Pressure Phase Equilibria for Polypropylene-Hydrocarbon Systems," *Ind. Eng. Chem. Res.* v. 39(12), pp. 4627-4633.

A bulk polymerization means a polymerization process in which the monomers and/or comonomers being polymerized are used as a solvent or diluent using little or no inert solvent or diluent. A small fraction of inert solvent might be used as a carrier for catalyst and scavenger. A bulk polymerization system contains less than about 25 wt % of inert solvent or diluent, such as less than about 10 wt %, such as less than about 1 wt %, such as 0 wt %.

Ligands

In one or more embodiments, the present disclosure provides one or more ligands that can be contained in a transition metal complex or catalyst, as discussed and described herein. A ligand can be represented by the Formula (I):

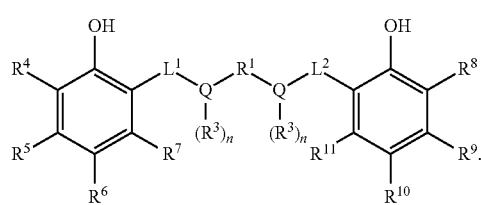

The group $R^1$ is a linker or bridge between the two Q groups. In some embodiments, $R^1$ is a substituted or unsubstituted linear, branched, cyclic, polycyclic, heterocyclic, or aromatic diyl linking the two Q groups. For example, $R^1$ can be a substituted or unsubstituted $C_1$-$C_{30}$ diyl, such as a substituted or unsubstituted $C_1$-$C_{18}$ diyl, a substituted or unsubstituted $C_1$-$C_{10}$ diyl, a substituted or unsubstituted $C_1$-$C_6$ diyl, or a substituted or unsubstituted $C_1$-$C_5$ diyl. In some examples, the $R^1$ can be or include an unsubstituted organic diyl group that can be or include methanediyl (—$CH_2$—), ethanediyl (—$CH_2CH_2$—), propanediyl (—$CH_2CH_2CH_2$—), butanediyl (—$CH_2(CH_2)_2CH_2$—), pentanediyl (—$CH_2(CH_2)_3CH_2$—), hexanediyl (—$CH_2(CH_2)_4CH_2$—), heptanediyl (—$CH_2(CH_2)_5CH_2$—), octanediyl (—$CH_2(CH_2)_6CH_2$—), nonanediyl (—$CH_2(CH_2)_7CH_2$—), decanediyl (—$CH_2(CH_2)_6CH_2$—), undecanediyl (—$CH_2(CH_2)_9CH_2$—), dodecanediyl (—$CH_2(CH_2)_{10}CH_2$—), isomers thereof, halide-substituted analogues thereof, or other substitutes thereof. In one or more examples, $R^1$ can be a substituted or unsubstituted linear or branched $C_1$-$C_6$ diyl, for example, an unsubstituted methanediyl, ethanediyl, propanediyl, a butanediyl, or a pentanediyl.

In other examples, $R^1$ can be a substituted or unsubstituted cyclic, polycyclic, heterocyclic, or aromatic $C_1$-$C_{18}$ or $C_1$-$C_{10}$ diyl. For example, $R^1$ can be or include a phenyl diyl, a benzyl diyl, a cyclohexyl diyl, a cyclooctyl diyl, or substitutes thereof. In some examples, the group $R^1$ can be or include a substituted or unsubstituted heterocyclic diyl group that can be or include one or more aminos, iminos, ethers, thioethers, silyls, boryls, phosphinos, phosphines, or any combination thereof.

Each Q is independently a Group 15 atom (e.g., N or P) or a Group 16 atom (e.g., O, S, or Se). In embodiments where Q is a Group 16 atom, $R^3$ is not present thereon. For example, each n is independently either 0 or 1, hence n is 0 if Q is a Group 16 atom or n is 1 if Q is a Group 15 atom. In one or more examples, Q is O, N, S, or P.

The linker $L^1$ is a substituted or unsubstituted methanediyl group,

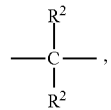

that is not part of an aromatic ring.

Each $R^2$ is independently a hydrogen, a halogen or halide (e.g., F, Br, Cl, or I), a substituted or unsubstituted $C_1$-$C_{40}$ hydrocarbyl, or a heteroatom-containing group. In one or more examples, the substituted or unsubstituted $C_1$-$C_{40}$ hydrocarbyl can be or include a substituted or unsubstituted branched $C_3$-$C_{40}$ hydrocarbyl or a substituted or unsubstituted cyclic, polycyclic, aromatic, or polyaromatic $C_4$-$C_{40}$ hydrocarbyl. In some examples, each $R^2$ is independently methyl, ethyl, ethenyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclohexyl, cyclooctyl, phenyl, benzyl, naphthyl, phenanthryl, anthracenyl, carbazolyl, fluorenyl, adamantly, indolyl, indolinyl, imidazolyl, indenyl, indanyl, isomers thereof, halide-substituted analogues thereof, or other substitutes thereof. The heteroatom-containing group can be or include amino, imino, ether, thioether, silyl, boryl, phosphino, or any combination thereof. In other examples, two or more adjacent $R^2$ groups are joined together to form a $C_4$-$C_{62}$ cyclic, polycyclic, or heterocyclic group that is not aromatic. For example, two or more adjacent $R^2$ groups are joined together to form a $C_5$-$C_{62}$, $C_{10}$-$C_{50}$, or $C_{12}$-$C_{40}$ cyclic, polycyclic, or heterocyclic group that is not aromatic.

The linker $L^2$ is a substituted or unsubstituted organic diyl group,

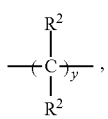

that is not part of an aromatic ring. The substituted or unsubstituted organic diyl group can have two or more —CR$_2$— groups, such as where y is an integer of 2, 3, 4, 5, 6, 7, 8, 9, 10, 11, or 12. For example, y can be an integer in a range of 2-12, 2-10, 2-8, or 2-5. In one or more examples, L$^2$ is ethanediyl (—CH$_2$CH$_2$—), propanediyl (—CH$_2$CH$_2$CH$_2$—), butanediyl (—CH$_2$(CH$_2$)$_2$CH$_2$—), pentanediyl (—CH$_2$(CH$_2$)$_3$CH$_2$—), hexanediyl (—CH$_2$(CH$_2$)$_4$CH$_2$—), heptanediyl (—CH$_2$(CH$_2$)$_5$CH$_2$—), octanediyl (—CH$_2$(CH$_2$)$_6$CH$_2$—), nonanediyl (—CH$_2$(CH$_2$)$_7$CH$_2$—), decanediyl (—CH$_2$(CH$_2$)$_8$CH$_2$—), undecanediyl (—CH$_2$(CH$_2$)$_9$CH$_2$—), dodecanediyl (—CH$_2$(CH$_2$)$_{10}$CH$_2$—), isomers thereof, or halide-substituted analogues thereof. In some examples, L$^1$ is an unsubstituted methanediyl and L$^2$ can be a substituted or unsubstituted ethanediyl.

In one or more embodiments, for both L$^1$ and L$^2$, each R$^2$ is independently a hydrogen or a substituted or unsubstituted C$_1$-C$_{10}$ hydrocarbyl. In some examples, L$^2$ has y as an integer of 2, 3, 4, or 5, and for both L$^1$ and L$^2$, each R$^2$ is independently a hydrogen or a substituted or unsubstituted C$_1$-C$_6$ hydrocarbyl. In other examples, L$^2$ has y as an integer of 2 or 3, each R$^2$ on L$^1$ is a hydrogen, or a substituted or unsubstituted C$_1$-C$_3$ hydrocarbyl, and each R$^2$ on L$^2$ is independently a hydrogen or a substituted or unsubstituted C$_1$-C$_3$ hydrocarbyl.

The bridged phenolate ligand is asymmetrical due to the different carbon chain lengths of L$^1$ and L$^2$. L$^1$ has fewer linker atoms than L$^2$ since L$^1$ is a methanediyl and L$^2$ is at least as long as an ethanediyl, or longer. The relatively high catalytic activity of the catalyst (the transition metal complex) and/or the catalyst system is attributed, at least in part, to the asymmetrical linkage or bridging provided by L$^1$ and L$^2$.

Each R$^3$ is independently a hydrogen, a substituted or unsubstituted C$_1$-C$_{40}$ hydrocarbyl, or a heteroatom-containing group. In one or more examples, the substituted or unsubstituted C$_1$-C$_{40}$ hydrocarbyl can be or include a substituted or unsubstituted branched C$_3$-C$_{40}$ hydrocarbyl or a substituted or unsubstituted cyclic, polycyclic, aromatic, or polyaromatic C$_4$-C$_{40}$ hydrocarbyl. The heteroatom-containing group can be or include amino, imino, ether, thioether, silyl, boryl, phosphino, or any combination thereof. In one or more examples, when Q is N, each R$^3$ is independently a hydrogen or a substituted or unsubstituted C$_1$-C$_{10}$ hydrocarbyl.

Each R$^4$, R$^5$, R$^6$, R$^7$, R$^8$, R$^9$, R$^{10}$, and R$^{11}$ is independently a hydrogen, a halogen or halide (e.g., F, Br, Cl, or I), a substituted or unsubstituted C$_1$-C$_{40}$ hydrocarbyl, or a heteroatom-containing group. In one or more examples, the substituted or unsubstituted C$_1$-C$_{40}$ hydrocarbyl can be or include a substituted or unsubstituted branched C$_3$-C$_{40}$ hydrocarbyl or a substituted or unsubstituted cyclic, polycyclic, aromatic, or polyaromatic C$_4$-C$_{40}$ hydrocarbyl. The heteroatom-containing group can be or include amino, imino, ether, thioether, silyl, boryl, phosphino, or any combination thereof. In one or more examples, each of the R$^4$, R$^5$, R$^6$, R$^7$, R$^8$, R$^9$, R$^{10}$, and R$^{11}$ groups can be or include methyl, ethyl, ethenyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclohexyl, cyclooctyl, phenyl, benzyl, naphthyl, phenanthryl, anthracenyl, carbazolyl, fluorenyl, adamantly, indolyl, indolinyl, imidazolyl, indenyl, indanyl, isomers thereof, halide-substituted analogues thereof, or other substitutes thereof. In other examples, two or more adjacent groups of R$^4$, R$^5$, R$^6$, R$^7$, R$^8$, R$^9$, R$^{10}$, and R$^{11}$ (R$^4$-R$^{11}$) are joined together to form a C$_4$-C$_{62}$ cyclic, polycyclic, heterocyclic, or aromatic group. For example, two or more adjacent R$^4$-R$^{11}$ groups are joined together to form a C$_5$-C$_{62}$, C$_{10}$-C$_{50}$, or C$_{12}$-C$_{40}$ cyclic, polycyclic, heterocyclic, or aromatic group.

In one or more examples, each R$^4$ and R$^8$ is independently halogen, phenyl, naphthyl, phenanthryl, anthracenyl, carbazolyl, fluorenyl, adamantly, indolyl, indolinyl, imidazolyl, indenyl, indanyl, or substitutes thereof. For example, R$^4$ can be carbazolyl, fluorenyl, adamantly, or a substitute thereof and R$^8$ can be a halogen, such as Br. In some examples, each R$^5$, R$^6$, R$^7$, R$^9$, R$^{10}$, and R$^{11}$ group can independently be a hydrogen or a substituted or unsubstituted linear or branched C$_1$-C$_{10}$ hydrocarbyl. For example, each R$^5$, R$^7$, R$^9$, and R$^{11}$ can be a hydrogen and each R$^6$ and R$^{10}$ can be a substituted or unsubstituted linear or branched C$_1$-C$_4$ hydrocarbyl.

In one or more embodiments, when the linker L$^1$ is an unsubstituted methanediyl group and the linker L$^2$ is an unsubstituted ethanediyl group, then the ligand can be represented by the Formula (III):

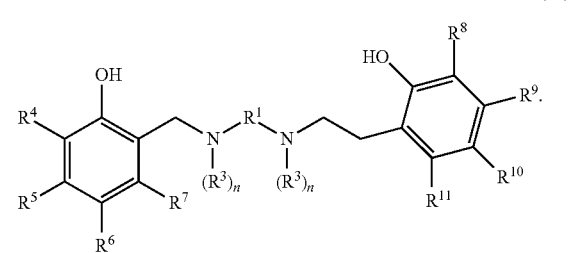

The ligand represented by Formula (III) can be referred to as a C$_1$,C$_2$-bridged ONNO ligand.

In one specific example, the ligand, which may be contained in a transition metal catalyst, can be represented by the Formula (IV(a)):

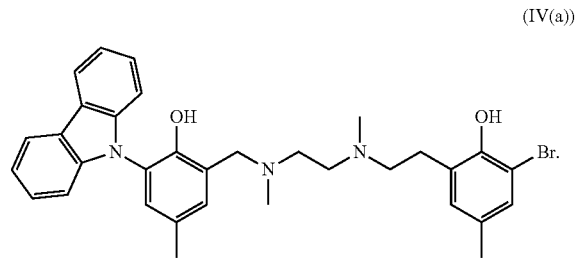

In other embodiments, when the linker or group R$^1$ is an unsubstituted ethanediyl group and both R$^3$ are methyl groups in the Formula (III), then the ligand can be represented by Formulas (IV(b)-(l)) as follows:

(IV(b))
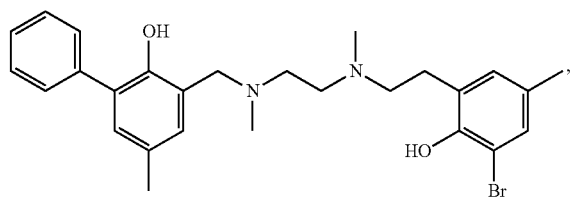
(IV(c))
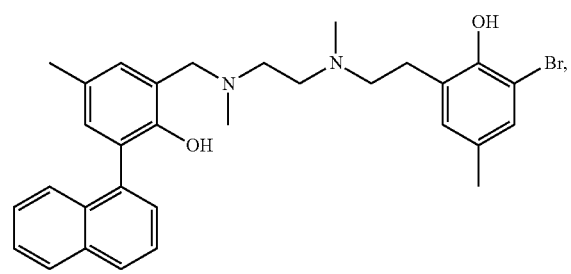
(IV(d))
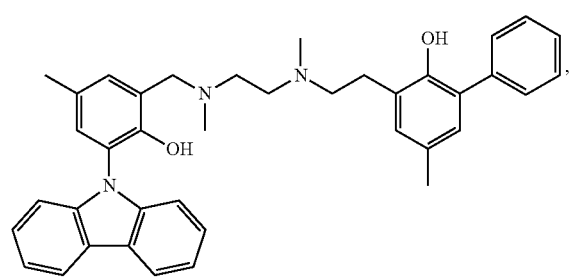
(IV(e))
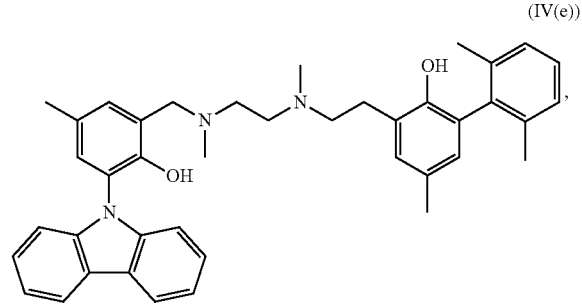
(IV(f))
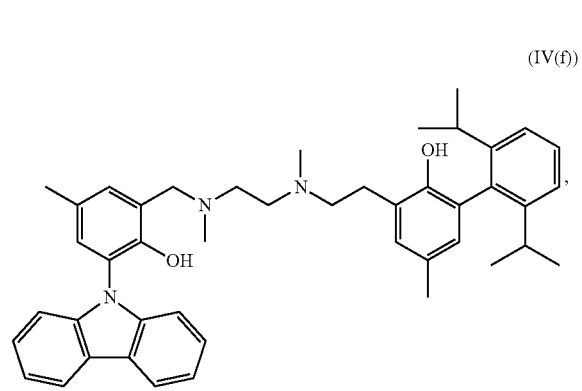
-continued
(IV(g))
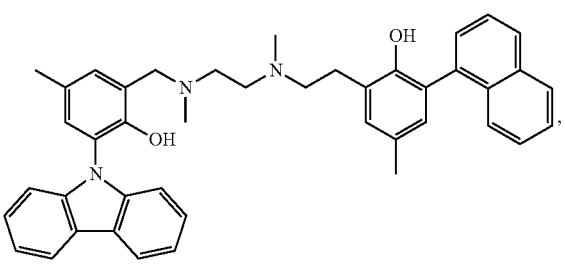
(IV(h))
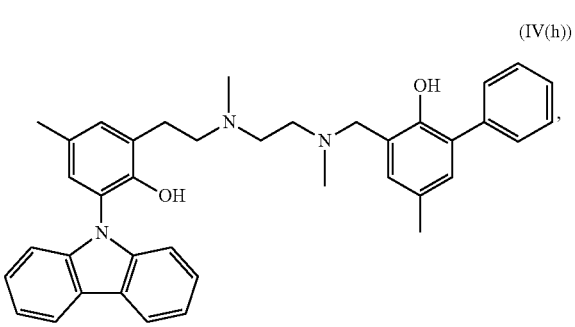
(IV(i))
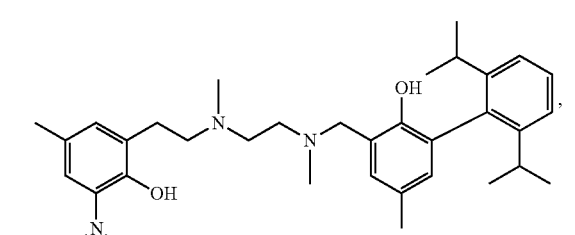
(IV(j))
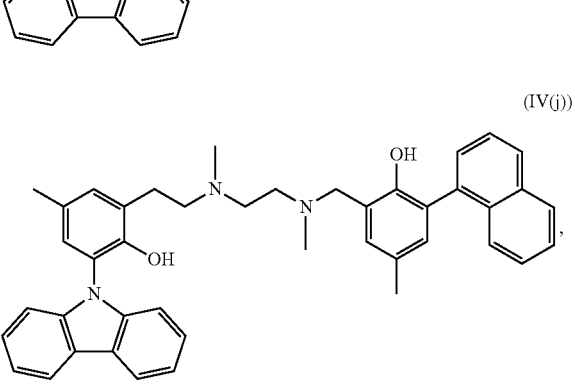
(IV(k))
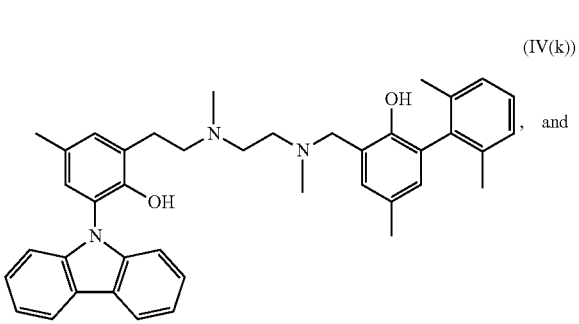
and -continued (IV(l))

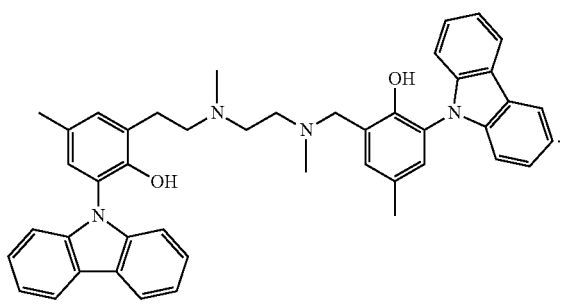

Catalysts

In one or more embodiments, the present disclosure provides catalysts that are bridged phenolate transition metal complexes that include any of the ligands represented by Formulas (I), (III), and (IV(a)-(l)) ligated to a transition metal atom. Without being bound by theory, the bridged phenolate ligand can undergo deprotonation of the phenol groups when ligating to the metal, as further discussed below. In one or more examples, the transition metal complex or catalyst is represented by Formula (II):

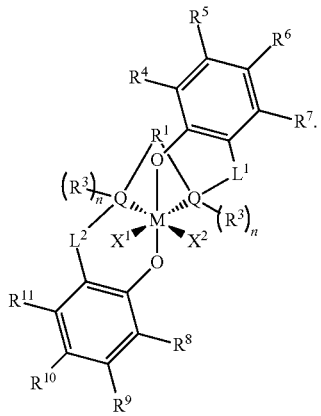

(II)

The metal M can be any transition metal. In one or more embodiments, the metal M is a Group 4 transition metal, such as titanium, hafnium, or zirconium. In one or more examples, M is hafnium or zirconium.

Each of $X^1$ and $X^2$ is independently a hydrogen, a halogen or halide (e.g., F, Br, Cl, or I), a substituted or unsubstituted $C_1$-$C_{40}$ hydrocarbyl, a heteroatom, or a heteroatom-containing group. In one or more examples, the substituted or unsubstituted $C_1$-$C_{40}$ hydrocarbyl can be or include a substituted or unsubstituted branched $C_3$-$C_{40}$ hydrocarbyl or a substituted or unsubstituted cyclic, polycyclic, aromatic, or polyaromatic $C_4$-$C_{40}$ hydrocarbyl. The heteroatom-containing group can be or include amino, imino, ether, thioether, silyl, boryl, phosphino, or any combination thereof. In other examples, $X^1$ and $X^2$ are joined together to form a $C_4$-$C_{62}$ cyclic, polycyclic, heterocyclic, or aromatic group that is not aromatic. For example, $X^1$ and $X^2$ are joined together to form a $C_5$-$C_{62}$, $C_{10}$-$C_{50}$, or $C_{12}$-$C_{40}$ cyclic, polycyclic, heterocyclic, or aromatic group.

In one or more examples, each of $X^1$ and $X^2$ is independently a substituted or unsubstituted $C_1$-$C_{20}$ hydrocarbyl. For example, each of $X^1$ and $X^2$ can independently be or include a substituted or unsubstituted $C_1$-$C_8$ alkyl, a phenyl, a benzyl, a naphthyl, a cyclohexyl, or halide-substituted analogues thereof. In some examples, each of $X^1$ and $X^2$ is a benzyl.

The group $R^1$ is a linker or bridge between the two Q groups. In some embodiments, $R^1$ is a substituted or unsubstituted linear, branched, cyclic, polycyclic, heterocyclic, or aromatic diyl linking the two Q groups. For example, $R^1$ can be a substituted or unsubstituted $C_1$-$C_{40}$ diyl, such as a substituted or unsubstituted $C_1$-$C_{30}$ diyl, as a substituted or unsubstituted $C_1$-$C_{18}$ diyl, a substituted or unsubstituted $C_1$-$C_{10}$ diyl, a substituted or unsubstituted $C_1$-$C_6$ diyl, or a substituted or unsubstituted $C_1$-$C_5$ diyl. In some examples, the $R^1$ can be or include an unsubstituted organic diyl group that can be or include methanediyl (—$CH_2$—), ethanediyl (—$CH_2CH_2$—), propanediyl (—$CH_2CH_2CH_2$—), butanediyl (—$CH_2(CH_2)_2CH_2$—), pentanediyl (—$CH_2(CH_2)_3CH_2$—), hexanediyl (—$CH_2(CH_2)_4CH_2$—), heptanediyl (—$CH_2(CH_2)_5CH_2$—), octanediyl (—$CH_2(CH_2)_6CH_2$—), nonanediyl (—$CH_2(CH_2)_7CH_2$—), decanediyl (—$CH_2(CH_2)_8CH_2$—), undecanediyl (—$CH_2(CH_2)_9CH_2$—), dodecanediyl (—$CH_2(CH_2)_{10}CH_2$—), isomers thereof, or halide-substituted analogues thereof. In one or more examples, $R^1$ can be a substituted or unsubstituted linear or branched $C_1$-$C_6$ diyl, for example, an unsubstituted methanediyl, ethanediyl, propanediyl, a butanediyl, a pentanediyl, or a hexanediyl.

In other examples, $R^1$ can be a substituted or unsubstituted cyclic, polycyclic, heterocyclic, or aromatic $C_1$-$C_{18}$ or $C_1$-$C_{10}$ diyl. For example, $R^1$ can be or include a phenyl diyl, a benzyl diyl, a cyclohexyl diyl, a cyclooctyl diyl, or substitutes thereof. In some examples, the group $R^1$ can be or include a substituted or unsubstituted heterocyclic diyl group that can be or include one or more aminos, iminos, ethers, thioethers, silyls, boryls, phosphinos, phosphines, or any combination thereof.

Each Q is independently a Group 15 atom (e.g., N or P) or a Group 16 atom (e.g., O, S, or Se). In embodiments where Q is a Group 16 atom, $R^3$ is not present thereon. For example, each n is independently either 0 or 1, hence n is 0 if Q is a Group 16 atom or n is 1 if Q is a Group 15 atom. In one or more examples, Q is O, N, S, or P.

The linker $L^1$ is a substituted or unsubstituted methanediyl group,

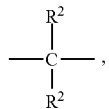

that is not part of an aromatic ring.

Each $R^2$ is independently a hydrogen, a halogen or halide (e.g., F, Br, Cl, or I), a substituted or unsubstituted $C_1$-$C_{40}$ hydrocarbyl, or a heteroatom-containing group. In one or more examples, the substituted or unsubstituted $C_1$-$C_{40}$ hydrocarbyl can be or include a substituted or unsubstituted branched $C_3$-$C_{40}$ hydrocarbyl or a substituted or unsubstituted cyclic, polycyclic, aromatic, or polyaromatic $C_4$-$C_{40}$ hydrocarbyl. In some examples, each $R^2$ is independently methyl, ethyl, ethenyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclohexyl, cyclooctyl, phenyl, benzyl, naphthyl, phenanthryl, anthracenyl, carbazolyl, fluorenyl, adamantly, indolyl, indolinyl, imidazolyl, indenyl, indanyl, isomers thereof, halide-substituted analogues thereof, or other substitutes thereof. The heteroatom-containing group can be or include amino, imino, ether, thioether, silyl, boryl, phosphino, or any combination thereof. In other examples, two or more adjacent $R^2$ groups are joined together to form a $C_4$-$C_{62}$ cyclic, polycyclic, or heterocyclic group that is not aromatic. For example, two or more adjacent $R^2$ groups are joined together to form a $C_5$-$C_{62}$, $C_{10}$-$C_{50}$, or $C_{12}$-$C_{40}$ cyclic, polycyclic, or heterocyclic group that is not aromatic.

The linker $L^2$ is a substituted or unsubstituted organic diyl group,

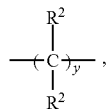

that is not part of an aromatic ring. The substituted or unsubstituted organic diyl group can have two or more —$CR_2$— groups, such as where y is an integer of 2, 3, 4, 5, 6, 7, 8, 9, 10, 11, or 12. For example, y can be an integer in a range of 2-12, 2-10, 2-8, or 2-5. In one or more examples, $L^2$ can be ethanediyl (—$CH_2CH_2$—), propanediyl (—$CH_2CH_2CH_2$—), butanediyl (—$CH_2(CH_2)_2CH_2$—), pentanediyl (—$CH_2(CH_2)_3CH_2$—), hexanediyl (—$CH_2(CH_2)_4CH_2$—), heptanediyl (—$CH_2(CH_2)_5CH_2$—), octanediyl (—$CH_2(CH_2)_6CH_2$—), nonanediyl (—$CH_2(CH_2)_7CH_2$—), decanediyl (—$CH_2(CH_2)_8CH_2$—), undecanediyl (—$CH_2(CH_2)_9CH_2$—), dodecanediyl (—$CH_2(CH_2)_{10}CH_2$—), isomers thereof, or halide-substituted analogues thereof. In some examples, $L^1$ can be an unsubstituted methanediyl and $L^2$ can be a substituted or unsubstituted ethanediyl.

In one or more embodiments, for both $L^1$ and $L^2$, each $R^2$ is independently a hydrogen or a substituted or unsubstituted $C_1$-$C_{10}$ hydrocarbyl. In some examples, $L^2$ can have y as an integer of 2, 3, 4, or 5, and for both $L^1$ and $L^2$, each $R^2$ is independently a hydrogen or a substituted or unsubstituted $C_1$-$C_5$ hydrocarbyl. In other examples, $L^2$ can have y as an integer of 2 or 3, each $R^2$ on $L^1$ is a hydrogen or a substituted or unsubstituted $C_1$-$C_3$ hydrocarbyl, and each $R^2$ on $L^2$ is independently a hydrogen or a substituted or unsubstituted $C_1$-$C_3$ hydrocarbyl.

Each $R^3$ is independently a hydrogen, a substituted or unsubstituted $C_1$-$C_{40}$ hydrocarbyl, or a heteroatom-containing group. In one or more examples, the substituted or unsubstituted $C_1$-$C_{40}$ hydrocarbyl can be or include a substituted or unsubstituted branched $C_3$-$C_{40}$ hydrocarbyl or a substituted or unsubstituted cyclic, polycyclic, aromatic, or polyaromatic $C_4$-$C_{40}$ hydrocarbyl. The heteroatom-containing group can be or include amino, imino, ether, thioether, silyl, boryl, phosphino, or any combination thereof. In one or more examples, when Q is N, each $R^3$ is independently a hydrogen or a substituted or unsubstituted $C_1$-$C_{10}$ hydrocarbyl.

Each of the $R^4$, $R^5$, $R^6$, $R^7$, $R^8$, $R^9$, $R^{10}$, and $R^{11}$ groups is independently a hydrogen, a halogen or halide (e.g., F, Br, Cl, or I), a substituted or unsubstituted $C_1$-$C_{40}$ hydrocarbyl, or a heteroatom-containing group. In one or more examples, the substituted or unsubstituted $C_1$-$C_{40}$ hydrocarbyl can be or include a substituted or unsubstituted branched $C_3$-$C_{40}$ hydrocarbyl or a substituted or unsubstituted cyclic, polycyclic, aromatic, or polyaromatic $C_4$-$C_{40}$ hydrocarbyl. The heteroatom-containing group can be or include amino, imino, ether, thioether, silyl, boryl, phosphino, or any combination thereof. In one or more examples, each of the $R^4$, $R^5$, $R^6$, $R^7$, $R^8$, $R^9$, $R^{10}$, and $R^{11}$ groups can be or include methyl, ethyl, ethenyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclohexyl, cyclooctyl, phenyl, benzyl, naphthyl, phenanthryl, anthracenyl, carbazolyl, fluorenyl, adamantly, indolyl, indolinyl, imidazolyl, indenyl, indanyl, isomers thereof, halide-substituted analogues thereof, or other substitutes thereof. In other examples, two or more adjacent groups of $R^4$, $R^5$, $R^6$, $R^7$, $R^8$, $R^9$, $R^{10}$, and $R^{11}$ ($R^4$-$R^{11}$) are joined together to form a $C_4$-$C_{62}$ cyclic, polycyclic, heterocyclic, or aromatic group. For example, two or more adjacent $R^4$-$R^{11}$ groups are joined together to form a $C_5$-$C_{62}$, $C_{10}$-$C_{50}$, or $C_{12}$-$C_{40}$ cyclic, polycyclic, heterocyclic, or aromatic group.

In one or more examples, each of $R^4$ and $R^8$ is independently halogen, phenyl, naphthyl, phenanthryl, anthracenyl, carbazolyl, fluorenyl, adamantly, indolyl, indolinyl, imidazolyl, indenyl, indanyl, or substitutes thereof. For example, $R^4$ can be carbazolyl, fluorenyl, adamantly, or a substitute thereof and $R^8$ can be a halogen, such as Br. In some examples, each of $R^5$, $R^6$, $R^7$, $R^9$, $R^{10}$, and $R^{11}$ group can independently be a hydrogen or a substituted or unsubstituted linear or branched $C_1$-$C_{10}$ hydrocarbyl. For example, each of $R^5$, $R^7$, $R^9$, and $R^{11}$ can be a hydrogen and each $R^6$ and $R^{10}$ can be a substituted or unsubstituted linear or branched $C_1$-$C_4$ hydrocarbyl.

In one or more embodiments, when each Q is a nitrogen, the linker $L^1$ is an unsubstituted methanediyl group, and the linker $L^2$ is an unsubstituted ethanediyl group, then the transition metal catalyst is represented by Formula (V):

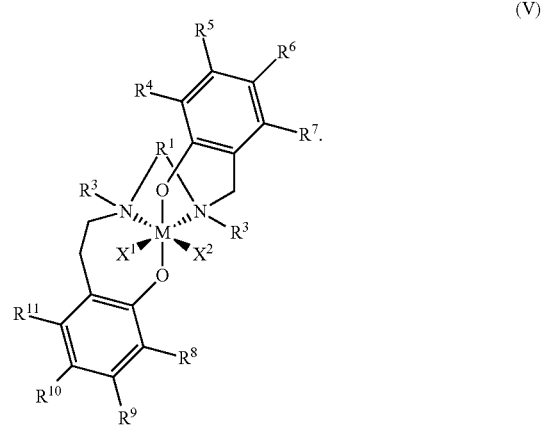

(V)

In one or more embodiments, when each Q is a nitrogen, the linker $L^1$ is an unsubstituted methanediyl group, the linker $L^2$ is an unsubstituted ethanediyl group, and $R^1$ is an unsubstituted ethanediyl group, then the transition metal catalyst is represented by Formula (VI):

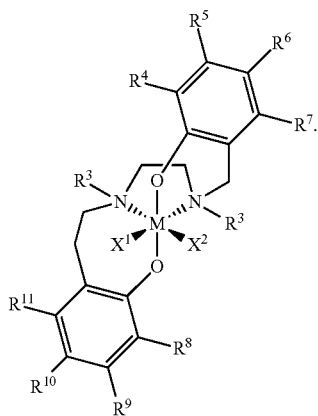
(VI)
In one specific example, the transition metal complex or catalyst is represented by Formula (VII(a)):
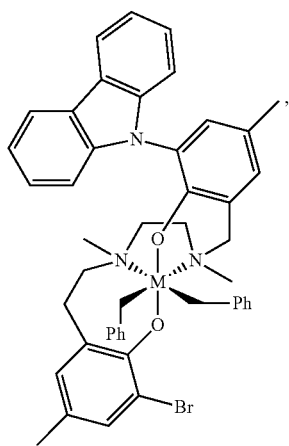
(VII(a))
where the metal M is titanium, hafnium, or zirconium.
In other embodiments, then the ligand can be represented by Formulas (VII(b)-(l)) as follows:
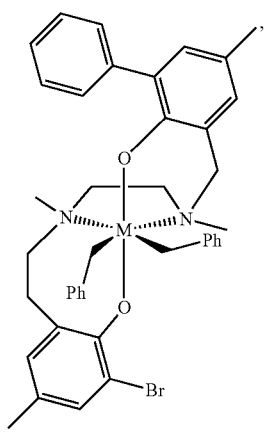
(VII(b))
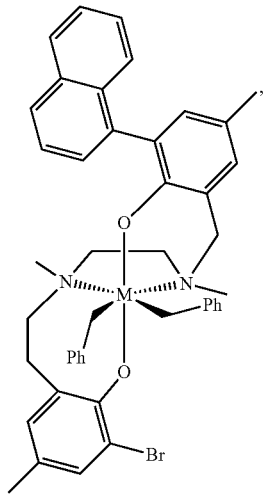
(VII(c))
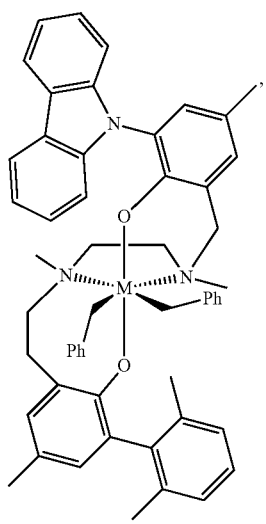
(VII(d))
(VII(e))

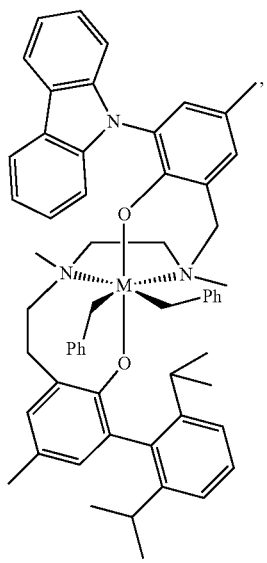 (VII(f))
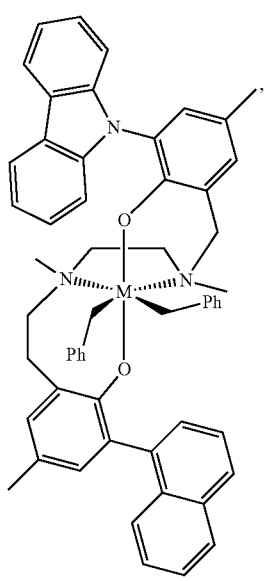 (VII(g))
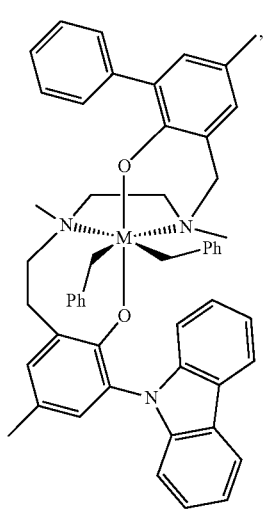 (VII(h))
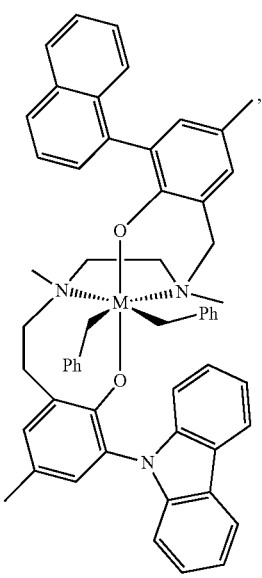 (VII(i))
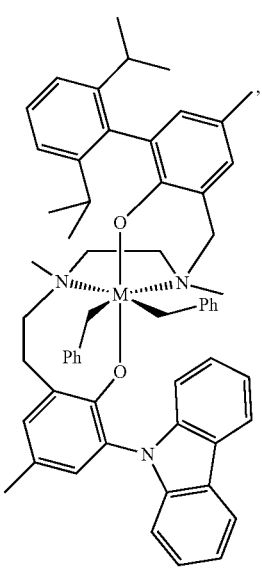 (VII(j))
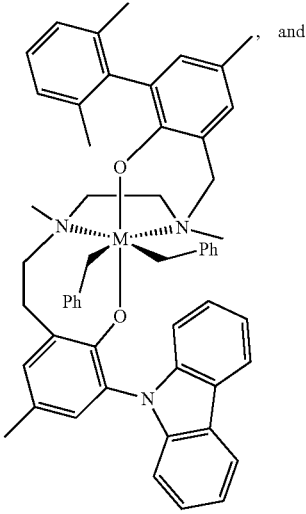 (VII(k))

-continued (VII(l))

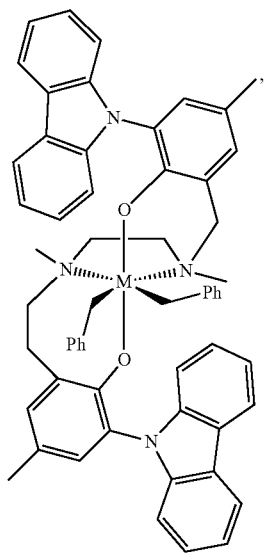

where the metal M is titanium, hafnium, or zirconium.

Methods to Prepare the Catalyst Compounds

All air sensitive syntheses are carried out in nitrogen or argon purged dry boxes. All solvents are available from commercial sources. Paraformaldehyde, 2-carbazolyl-4-methylphenol, N,N-dimethylformamide (DMF), triethylamine, N,N'-dimethylethylene-1,2-diamine, sodium cyanoborohydride, acetic acid, 2-bromo-4-methylphenol, allyl bromide, potassium carbonate, methoxymethyl chloride (MOM-Cl), toluene, tetrabenzyl hafnium, tetrabenzyl zirconium, and other precursors, reagents, and solvents are available from commercial sources. Ozone is generated by an ozone generator.

Generally, ligands of Formulas (I), (III), and (IV(a)-(l)) can be synthesized according to the schematic reaction procedure described in Schemes 1-3 and transition metal catalysts of Formulas (II), (V), (VI), (VII(a)-(l)) can be synthesized according to the schematic reaction procedure described in Scheme 4.

As shown in Scheme 1: (i) 2-carbazolyl-4-methylphenol is treated with paraformaldehyde to produce 2-carbazolyl-4-methyl-5-methenyl-oxo-phenol; (ii) 2-carbazolyl-4-methyl-6-methenyl-oxo-phenol is treated with N,N'-dimethylethylene-1,2-diamine to produce Compound A 2-carbazolyl-4-methyl-6-methene-(dimethyl-ethylenediamine)-phenol.

Scheme 1

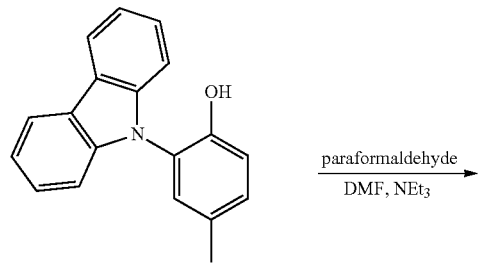

paraformaldehyde
DMF, NEt₃

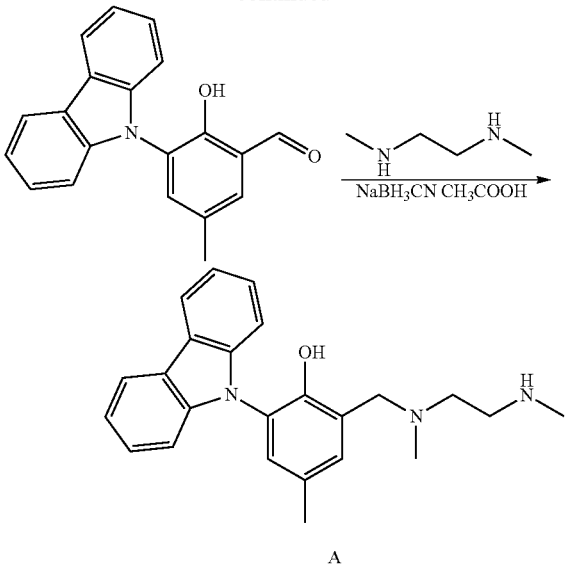

A

As shown in Scheme 2: (i) 2-bromo-4-methylphenol is treated with allyl bromide to produce 1-(allyloxy)-2-bromo-4-methylbenzene; (ii) 1-(allyloxy)-2-bromo-4-methylbenzene is heated to produce 2-bromo-4-methyl-6-allylphenol; (iii) 2-bromo-4-methyl-6-allylphenol is treated with methoxymethyl (MOM) chloride to produce 1-(MOM-oxy)-2-bromo-4-methyl-5-allylbenzene; and (iv) 1-(MOM-oxy)-2-bromo-4-methyl-6-allylbenzene is treated with ozone to produce Compound B 1-(MOM-oxy)-2-bromo-4-methyl-6-propenyl-oxo-benzene.

Scheme 2

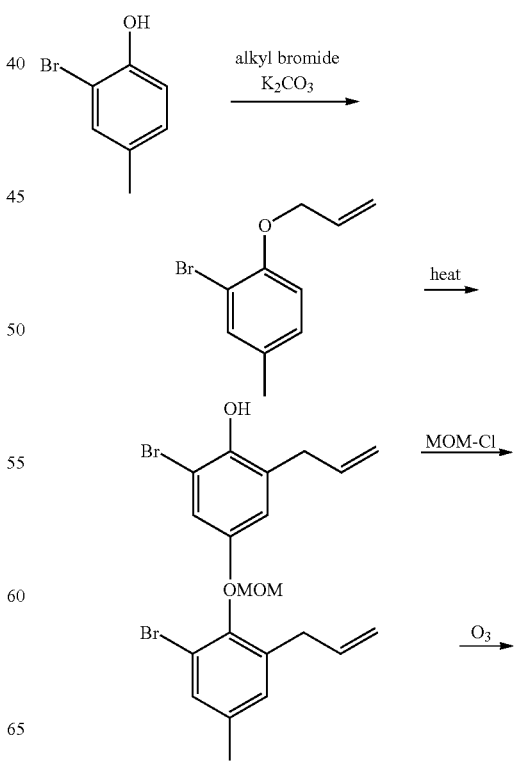

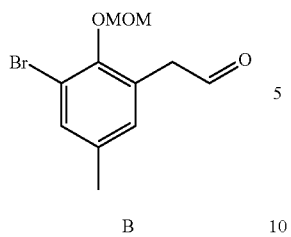

B

As shown in Scheme 3: Compound A 2-carbazolyl-4-methyl-6-methene-(dimethyl-ethylenediamine)-phenol and Compound B 1-(MOM-oxy)-2-bromo-4-methyl-6-propenyl-oxo-benzene in the presence sodium cyanoborohydride and acetic acid produce the ligand of Formula (III).

Scheme 3

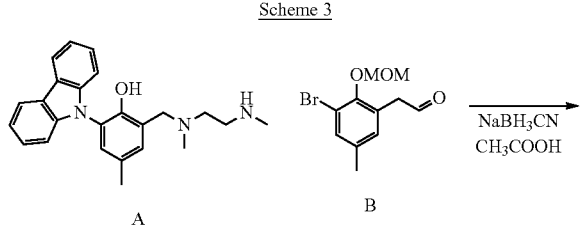

(III)

As shown in Scheme 4: The ligand of Formula (III) and a tetrabenzyl metal (Zr or Hf) in toluene to produce the transition metal catalysts of Formula (VII(a)), where M is zirconium or hafnium.

Scheme 4

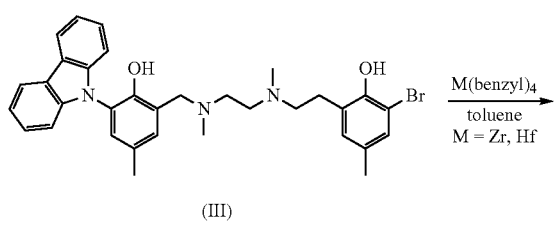

(III)

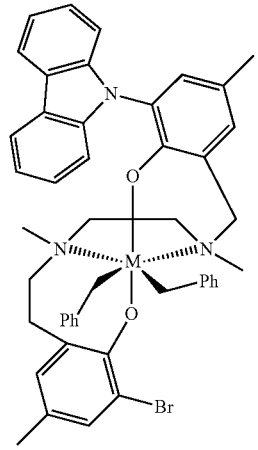

(VII(a))

Activators

After the catalysts have been synthesized, catalyst systems may be formed by combining the catalysts with activators in any suitable manner, including by supporting them for use in slurry or gas phase polymerization. The catalyst systems may also be added to or generated in solution polymerization or bulk polymerization (in the monomer, such as, without solvent). The catalyst system typically contains a transition metal complex as described above and an activator such as alumoxane or a non-coordinating anion activator. Activation may be performed using alumoxane solution including an alkyl alumoxane such as methyl alumoxane, referred to as MAO, as well as modified MAO, referred to herein as MMAO, which contains some higher alkyl groups to improve the solubility. MAO can be purchased from Albemarle Corporation, Baton Rouge, La., typically in a 10 wt % solution in toluene. In one or more examples, activators that can be used in the catalyst system can be or include one or more alumoxanes, one or more aluminum alkyls, and other aluminum compounds. Exemplary activators that can be used in the catalyst system can be or include, but are not limited to, methyl alumoxane, ethyl alumoxane, isobutyl alumoxane, isobutyl alumoxane, trimethyl aluminum, triethyl aluminum, tripropyl aluminum, tributyl aluminum, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetra(perfluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, isomers thereof, substitutes thereof, or any combination thereof.

When an alumoxane or modified alumoxane is used, the catalyst-to-activator molar ratio is from about 1:3,000 to about 10:1; such as about 1:2,000 to about 10:1; such as about 1:1,000 to about 10:1; such as about 1:500 to about 1:1; such as about 1:300 to about 1:1; such as about 1:200 to about 1:1; such as about 1:100 to about 1:1; such as about 1:50 to about 1:1; such as about 1:10 to about 1:1. When the activator is an alumoxane (modified or unmodified), some embodiments select the maximum amount of activator at a 5,000-fold molar excess over the catalyst (per metal catalytic site). The minimum activator-to-catalyst ratio can be 1:1 molar ratio.

Another useful alumoxane is solid polymethylaluminoxane as described in U.S. Pat. Nos. 8,404,880; 8,975,209; and 9,340,630.

Activation may also be performed using non-coordinating anions, referred to as NCA's, of the type, for example, described in EP 0277003 A1 and EP 0277004 A1. NCA may be added in the form of an ion pair using, for example, [DMAH]+[NCA]− in which the N,N-dimethylanilinium (DMAH) cation reacts with a basic leaving group on the transition metal complex to form a transition metal complex cation and [NCA]−. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis (pentafluorophenyl)borate ($[PhNMe_2H]B(C_6F_5)_4$) and N,N-dimethylanilinium tetrakis (heptafluoronaphthyl)borate, where Ph is phenyl, and Me is methyl.

Additionally activators useful herein include those described in U.S. Pat. No. 7,247,687 at column 169, line 50 to column 174, line 43, particularly column 172, line 24 to column 173, line 53.

In another embodiment, the non-coordinating anion activator is represented by the following formula (1):

$$(Z)^{d+}(A^{d-}) \qquad (1)$$

wherein Z is (L-H) or a reducible Lewis acid, L is a neutral Lewis base, H is hydrogen and $(L-H)^+$ is a Brønsted acid; $A^{d-}$ is a non-coordinating anion having the charge d−; and d is an integer from 1 to 3.

When Z is (L-H) such that the cation component is $(L-H)^{d+}$, the cation component may include Brønsted acids such as protonated Lewis bases capable of protonating a moiety, such as an alkyl or aryl, from the catalyst precursor, resulting in a cationic transition metal species, or the activating cation $(L-H)^{d+}$ is a Brønsted acid, capable of donating a proton to the catalyst precursor resulting in a transition metal cation, including ammoniums, oxoniums, phosphoniums, silyliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, it may be represented by the formula: ($Ar_3C+$), where Ar is aryl or aryl substituted with a heteroatom, or a $C_1$ to $C_{40}$ hydrocarbyl, the reducible Lewis acid may be represented by the formula: ($Ph_3C+$), where Ph is phenyl or phenyl substituted with a heteroatom, and/or a $C_1$ to $C_{40}$ hydrocarbyl. In some examples, the reducible Lewis acid is triphenyl carbenium.

Embodiments of the anion component $A^{d-}$ include those having the formula $[M^k+Q^n]^{d-}$ wherein k is 1, 2, or 3; n is 1, 2, 3, 4, 5 or 6, or 3, 4, 5 or 6; n−k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, the Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable Ad− components also include diboron compounds as disclosed in U.S. Pat. No. 5,447,895, which is fully incorporated herein by reference.

In an embodiment in any of the NCA's represented by Formula 1 described above, the anion component Ad− is represented by the formula [M*k*+Q*n*]d*− wherein k* is 1, 2, or 3; n* is 1, 2, 3, 4, 5, or 6 (or 1, 2, 3, or 4); n*-k*=d*; M* is boron; and Q* is independently selected from hydride, bridged or unbridged dialkylamido, halogen, alkoxide, aryloxide, hydrocarbyl radicals, the Q* having up to 20 carbon atoms with the proviso that in not more than 1 occurrence is Q* a halogen.

The present disclosure also provides a method to polymerize olefins including contacting olefins (such as propylene) with a catalyst complex as described above and an NCA activator represented by the Formula (2):

$$R_nM^{**}(ArNHal)^{4-n} \qquad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA containing an anion of Formula 2 also contains a suitable cation that is essentially non-interfering with the ionic catalyst complexes formed with the transition metal compounds, or the cation is Zd+ as described above.

In one or more embodiments, in any of the NCA's containing an anion represented by Formula 2 described above, R is a $C_1$ to $C_{30}$ hydrocarbyl radical. In an embodiment, $C_1$ to $C_{30}$ hydrocarbyl radicals may be substituted with one or more $C_1$ to $C_{20}$ hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl radicals; —SRa, —NRa$_2$, and —PRa$_2$, where each Ra is independently a monovalent $C_4$ to $C_{20}$ hydrocarbyl radical having a molecular volume greater than or equal to the molecular volume of an isopropyl substitution or a $C_4$ to $C_{20}$ hydrocarbyl substituted organometalloid having a molecular volume greater than or equal to the molecular volume of an isopropyl substitution.

In one or more embodiments, in any of the NCA's containing an anion represented by Formula 2 described above, the NCA also includes cation containing a reducible Lewis acid represented by the formula: ($Ar_3C+$), where Ar is aryl or aryl substituted with a heteroatom, and/or a $C_1$ to $C_{40}$ hydrocarbyl, or the reducible Lewis acid represented by the formula: ($Ph_3C+$), where Ph is phenyl or phenyl substituted with one or more heteroatoms, and/or $C_1$ to $C_{40}$ hydrocarbyls.

In one or more embodiments in any of the NCA's containing an anion represented by Formula 2 described above, the NCA may also contain a cation represented by the formula, $(L-H)^{d+}$, wherein L is an neutral Lewis base; H is hydrogen; (L-H) is a Brønsted acid; and d is 1, 2, or 3, or $(L-H)^{d+}$ is a Brønsted acid selected from ammoniums, oxoniums, phosphoniums, silyliums, and mixtures thereof.

Further examples of useful activators include those disclosed in U.S. Pat. Nos. 7,297,653 and 7,799,879, which are fully incorporated by reference herein.

In one or more embodiments, an activator can be or include a salt of a cationic oxidizing agent and a noncoordinating, compatible anion represented by the Formula (3):

$$(OX^{e+})_d(A^{d-})_e \qquad (3)$$

wherein $OX^{e+}$ is a cationic oxidizing agent having a charge of e+; e is 1, 2 or 3; d is 1, 2 or 3; and $A^{d-}$ is a non-coordinating anion having the charge of d− (as further described above). Examples of cationic oxidizing agents include: ferrocenium, hydrocarbyl-substituted ferrocenium, $Ag^+$, or $Pb^{+2}$. Suitable embodiments of $A^{d-}$ include tetrakis(pentafluorophenyl)borate.

Activators useful in catalyst systems can be or include one or more of: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

Suitable activators also include: N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In one or more embodiments, the activator can be or include one or more of a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In one or more embodiments, an activator can be or include one or more of N,N-dimethylanilinium tetra(perfluorophenyl)borate; N,N-dimethylanilinium tetrakis(perfluoronaphthyl)borate; N,N-dimethylanilinium tetrakis(perfluorobiphenyl)borate; N,N-dimethylanilinium tetrakis(3,5-bis(trifluoromethyl)phenyl)borate; triphenylcarbenium tetrakis(perfluoronaphthyl)borate; triphenylcarbenium tetrakis(perfluorobiphenyl)borate; triphenylcarbenium tetrakis(3,5-bis(trifluoromethyl)phenyl)borate; triphenylcarbenium tetra(perfluorophenyl)borate; trimethylammonium tetrakis(perfluoronaphthyl)borate; triethylammonium tetrakis(perfluoronaphthyl)borate; tripropylammonium tetrakis(perfluoronaphthyl)borate; tri(n-butyl)ammonium tetrakis(perfluoronaphthyl)borate; tri(t-butyl)ammonium tetrakis(perfluoronaphthyl)borate; N,N-diethylanilinium tetrakis(perfluoronaphthyl)borate; N,N-dimethyl-(2,4,6-trimethylanilinium) tetrakis(perfluoronaphthyl)borate; and tropillium tetrakis(perfluoronaphthyl)borate.

In one or more embodiments, two NCA activators may be used in the polymerization and the molar ratio of the first NCA activator to the second NCA activator can be any ratio. In one or more embodiments, the molar ratio of the first NCA activator to the second NCA activator is 0.01:1 to 10,000:1, or 0.1:1 to 1,000:1, or 1:1 to 100:1.

In some embodiments, the NCA activator-to-catalyst ratio is a 1:1 molar ratio, or 0.1:1 to 100:1, or 0.5:1 to 200:1, or 1:1 to 500:1 or 1:1 to 1,000:1. In one or more embodiments, the NCA activator-to-catalyst ratio is 0.5:1 to 10:1, or 1:1 to 5:1.

In one or more embodiments, the transition metal catalysts can be combined with combinations of alumoxanes and NCA's (see for example, U.S. Pat. Nos. 5,153,157, 5,453,410, EP 0573120 B1, WO 1994/007928, and WO 1995/014044 which discuss the use of an alumoxane in combination with an ionizing activator, all of which are incorporated by reference herein).

In some embodiments, when an NCA (such as an ionic or neutral stoichiometric activator) is used, the catalyst-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Likewise, a co-activator, such as a group 1, 2, or 13 organometallic species (e.g., an alkyl aluminum compound such as tri-n-octyl aluminum), may be used in the catalyst system herein. The catalyst-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Support Materials

In embodiments herein, the catalyst system can include an inert support material. In one or more embodiments, the supported material is a porous support material, for example, talc, or inorganic oxides. Other support materials include zeolites, clays, organoclays, or any other suitable organic or inorganic support material and the like, or mixtures thereof.

In one or more embodiments, the support material is an inorganic oxide. Suitable inorganic oxide materials for use in transition metal catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, functionalized polyolefins, such as polyethylene. Supports include magnesia, titania, zirconia, montmorillonite, phyllosilicate, zeolites, talc, clays, and the like. Also, combinations of these support materials may be used, for example, silica-chromium, silica-alumina, silica-titania, and the like. Support materials can include, but are not limited to $Al_2O_3$, $ZrO_2$, $SiO_2$, $SiO_2/Al_2O_3$, $SiO_2/TiO_2$, silica clay, silicon oxide/clay, or any mixture thereof.

The support material, such as an inorganic oxide, can have a surface area in the range from about 10 $m^2/g$ to about 700 $m^2/g$, pore volume in the range from about 0.1 cc/g to about 4.0 cc/g and average particle size in the range from about 5 μm to about 500 μm. In one or more embodiments, the surface area of the support material is in the range from about 50 $m^2/g$ to about 500 $m^2/g$, pore volume of from about 0.5 cc/g to about 3.5 cc/g and average particle size of from about 10 μm to about 200 μm. In one or more embodiments, the surface area of the support material is in the range is from about 100 $m^2/g$ to about 400 $m^2/g$, pore volume from about 0.8 cc/g to about 3.0 cc/g and average particle size is from about 5 μm to about 100 μm. The average pore size of the support material useful in the present disclosure is in the range from 10 Å to 1,000 Å, such as 50 Å to about 500 Å, such as 75 Å to about 350 Å. In some embodiments, the support material is a high surface area, amorphous silica (surface area=300 m$^2$/gm; pore volume of 1.65 cm$^3$/gm). Silicas are marketed under the tradenames of DAVISON 952 or DAVISON 955 by the Davison Chemical Division of W.R. Grace and Company. In other embodiments, DAVISON 948 is used.

The support material should be dry, that is, substantially free of absorbed water. Drying of the support material can be effected by heating or calcining at about 100° C. to about 1,000° C., such as at least about 600° C. When the support material is silica, it is heated to at least 200° C., such as about 200° C. to about 850° C., such as at about 600° C.; and for a time of about 1 minute to about 100 hours, from about 12 hours to about 72 hours, or from about 24 hours to about 60 hours. The calcined support material should have at least some reactive hydroxyl (OH) groups to produce supported catalyst systems of the present disclosure. The calcined support material is then contacted with at least one polymerization catalyst containing one or more transition metal catalyst and an activator.

The support material, having reactive surface groups, typically hydroxyl groups, is slurried in a non-polar solvent and the resulting slurry is contacted with a solution of a transition metal catalyst and an activator. In some embodiments, the slurry of the support material is first contacted with the activator for a period of time in the range from about 0.5 hours to about 24 hours, from about 2 hours to about 16 hours, or from about 4 hours to about 8 hours. The solution of the transition metal catalyst is then contacted with the isolated support/activator. In some embodiments, the supported catalyst system is generated in situ. In one or more embodiments, the slurry of the support material is first contacted with the catalyst compound for a period of time in the range from about 0.5 hours to about 24 hours, from about 2 hours to about 16 hours, or from about 4 hours to about 8 hours. The slurry of the supported transition metal catalyst is then contacted with the activator solution.

The mixture of the catalyst, activator and support is heated to about 0° C. to about 70° C., such as to about 23° C. to about 60° C., such as at room temperature. Contact times typically range from about 0.5 hours to about 24 hours, from about 2 hours to about 16 hours, or from about 4 hours to about 8 hours.

Suitable non-polar solvents are materials in which all of the reactants used herein, e.g., the activator, and the catalyst compound, are at least partially soluble and which are liquid at room temperature. Non-limiting example non-polar solvents are alkanes, such as isopentane, hexane, n-heptane, octane, nonane, and decane, cycloalkanes, such as cyclohexane, aromatics, such as benzene, toluene, and ethylbenzene.

In one or more embodiments, the support material contains a support material treated with an electron-withdrawing anion. The support material can be silica, alumina, silica-alumina, silica-zirconia, alumina-zirconia, aluminum phosphate, heteropolytungstates, titania, magnesia, boria, zinc oxide, mixed oxides thereof, or mixtures thereof; and the electron-withdrawing anion is selected from fluoride, chloride, bromide, phosphate, triflate, bisulfate, sulfate, or any combination thereof.

The electron-withdrawing component used to treat the support material can be any component that increases the Lewis or Brønsted acidity of the support material upon treatment (as compared to the support material that is not treated with at least one electron-withdrawing anion). In one or more embodiments, the electron-withdrawing component is an electron-withdrawing anion derived from a salt, an acid, or other compound, such as a volatile organic compound, that serves as a source or precursor for that anion. Electron-withdrawing anions can be sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or mixtures thereof, or combinations thereof. An electron-withdrawing anion can be fluoride, chloride, bromide, phosphate, triflate, bisulfate, or sulfate, or any combination thereof, at least one embodiment of this disclosure. In one or more embodiments, the electron-withdrawing anion is sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof.

Thus, for example, the support material suitable for use in the catalyst systems of the present disclosure can be one or more of fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or combinations thereof. In one or more embodiments, the activator-support can be or include fluorided alumina, sulfated alumina, fluorided silica-alumina, sulfated silica-alumina, fluorided silica-coated alumina, sulfated silica-coated alumina, phosphated silica-coated alumina, or combinations thereof. In another embodiment, the support material includes alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, or combinations thereof. Further, any of these activator-supports optionally can be treated with a metal ion.

Exemplary cations suitable for use in the present disclosure in the salt of the electron-withdrawing anion include ammonium, trialkyl ammonium, tetraalkyl ammonium, tetraalkyl phosphonium, H$^+$, [H(OEt$_2$)$_2$]$^+$, or combinations thereof.

Further, combinations of one or more different electron-withdrawing anions, in varying proportions, can be used to tailor the specific acidity of the support material to a desired level. Combinations of electron-withdrawing components can be contacted with the support material simultaneously or individually, and in any order that provides a desired chemically-treated support material acidity. For example, in one or more embodiments, two or more electron-withdrawing anion source compounds in two or more separate contacting steps.

In one or more embodiments, a process by which a chemically-treated support material is prepared can include contacting a selected support material, or combination of support materials, with a first electron-withdrawing anion source compound to form a first mixture; such first mixture can be calcined and then contacted with a second electron-withdrawing anion source compound to form a second mixture; the second mixture can then be calcined to form a treated support material. In such a process, the first and second electron-withdrawing anion source compounds can be either the same or different compounds.

The method by which the oxide is contacted with the electron-withdrawing component, typically a salt or an acid of an electron-withdrawing anion, can include gelling, co-gelling, impregnation of one compound onto another, or combinations thereof. Following a contacting method, the contacted mixture of the support material, electron-withdrawing anion, and optional metal ion, can be calcined.

According to another embodiment of the present disclosure, the support material can be treated by a process that includes: (i) contacting a support material with a first electron-withdrawing anion source compound to form a first mixture; (ii) calcining the first mixture to produce a calcined first mixture; (iii) contacting the calcined first mixture with a second electron-withdrawing anion source compound to form a second mixture; and (iv) calcining the second mixture to form the treated support material.

Polymerization Processes

In embodiments herein, the present disclosure provides polymerization processes where monomer (e.g., ethylene and/or propylene), and optionally comonomer, are contacted with a catalyst system containing one or more transition metal catalysts and one or more activators, as described above. The catalyst compound and activator may be combined in any order, and are combined typically prior to contacting with the monomer.

In one or more embodiments, a polymerization process includes a) contacting one or more olefin monomers with a catalyst system containing: i) an activator and ii) a catalyst compound. The activator may be an alumoxane or a non-coordination anion activator. The one or more olefin monomers can be or include, but are not limited to, ethylene, propylene, butylene, or any combination thereof. The polymerization process further includes heating the one or more olefin monomers and the catalyst system to 70° C. or more to form polyethylene, polypropylene, or a copolymer containing both polyethylene and polypropylene.

Monomers useful herein include substituted or unsubstituted $C_2$ to $C_{40}$ alpha olefins, such as $C_2$ to $C_{20}$ alpha olefins, such as $C_2$ to $C_{12}$ alpha olefins, such as ethylene, propylene, butene, pentene, hexene, heptene, octene, nonene, decene, undecene, dodecene and isomers thereof. In one or more embodiments, the monomer contains ethylene and an optional comonomers containing one or more ethylene or $C_4$ to $C_{40}$ olefins, such as $C_4$ to $C_{20}$ olefins, such as $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In one or more embodiments, the monomer contains ethylene and an optional comonomers containing one or more $C_3$ to $C_{40}$ olefins, such as $C_4$ to $C_{20}$ olefins, such as $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, such as hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, such as norbornene, norbornadiene, and dicyclopentadiene.

In one or more embodiments, one or more dienes are present in the polymer produced herein at up to 10 weight % (wt %), such as at about 0.00001 wt % to about 1.0 wt %, such as about 0.002 wt % to about 0.5 wt %, such as about 0.003 wt % to about 0.2 wt %, based upon the total weight of the composition. In some embodiments 500 ppm or less of diene is added to the polymerization, such as 400 ppm or less, such as 300 ppm or less. In other embodiments, at least 50 ppm of diene is added to the polymerization, or 100 ppm or more, or 150 ppm or more.

Diolefin monomers include any hydrocarbon structure, such as $C_4$ to $C_{30}$, having at least two unsaturated bonds, wherein at least two of the unsaturated bonds are readily incorporated into a polymer by either a stereospecific or a non-stereospecific catalyst(s). The diolefin monomers can be selected from alpha, omega-diene monomers (e.g., di-vinyl monomers). The diolefin monomers are linear di-vinyl monomers, such as those containing from 4 carbon atoms to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1,000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes of the present disclosure can be carried out in any suitable manner. Any suitable suspension, homogeneous, bulk, solution, slurry, or gas phase polymerization process can be used. Such processes can be run in a batch, semi-batch, or continuous mode. Homogeneous polymerization processes and slurry processes can be performed. For example, a homogeneous polymerization process is one where at least 90 wt % of the product is soluble in the reaction media. A bulk homogeneous process can be used. For example, a bulk process is one where monomer concentration in all feeds to the reactor is 70 volume % or more. Alternately, no solvent or diluent is present or added in the reaction medium, (except for the small amounts used as the carrier for the catalyst system or other additives, or amounts typically found with the monomer; e.g., propane in propylene). In one or more embodiments, the process is a slurry polymerization process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_4$-$C_{10}$ alkanes, chlorobenzene, and aromatic and alkylsubstituted aromatic compounds, such as benzene, toluene, mesitylene, and xylene.

Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In one or more embodiments, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In one or more embodiments, the solvent is not aromatic, such that aromatics are present in the solvent at less than 1 wt %, such as less than 0.5 wt %, such as less than 0 wt % based upon the weight of the solvents.

In one or more embodiments, the feed concentration of the monomers and comonomers for the polymerization is 60 vol % solvent or less, such as 40 vol % or less, such as 20 vol % or less, based on the total volume of the feedstream. The polymerization can be performed in a bulk process.

Polymerizations can be performed at any temperature and/or pressure suitable to obtain the desired polymers, such as ethylene and or propylene polymers. Typical temperatures and/or pressures include a temperature of about 0° C. to about 300° C., such as about 20° C. to about 200° C., such as about 35° C. to about 150° C., such as about 40° C. to about 120° C., such as about 45° C. to about 80° C., for example about 74° C., and at a pressure of about 0.05 MPa to about 1,500 MPa, about 1.7 MPa to about 30 MPa, or in some embodiments, such as under supercritical conditions, about 15 MPa to about 1,500 MPa.

In a typical polymerization, the run time of the reaction is up to 300 minutes, such as in the range from about 5 minutes to about 250 minutes, such as about 10 minutes to about 120 minutes.

In one or more embodiments, hydrogen is present in the polymerization reactor at a partial pressure of about 0.001 psig to about 50 psig (about 0.007 kPa to about 345 kPa), such as from about 0.01 psig to about 25 psig (about 0.07 kPa to about 172 kPa), such as about 0.1 psig to about 10 psig (about 0.7 kPa to about 70 kPa).

In one or more embodiments, the productivity of a catalyst of the present disclosure is from about 1,000 gPgcat$^{-1}$ hr$^{-1}$ to about 20,000 gPgcat$^{-1}$ hr$^{-1}$, such as from about 2,000 gPgcat$^{-1}$ hr$^{-1}$ to about 15,000 gPgcat$^{-1}$ hr$^{-1}$, such as from about 4,000 gPgcat$^{-1}$ hr$^{-1}$ to about 14,000 gPgcat$^{-1}$ hr$^{-1}$, such as from about 6,000 gPgcat$^{-1}$ hr$^{-1}$ to about 13,000 gPgcat$^{-1}$ hr$^{-1}$, such as from about 8,000 gPgcat$^{-1}$ hr$^{-1}$ to about 12,000 gPgcat$^{-1}$ hr$^{-1}$.

In one or more embodiments, the catalyst system, the transition metal complex, and/or the catalyst has a catalytic activity of about 10 kg/mmol-hr, about 20 kg/mmol-hr, about 40 kg/mmol-hr, about 50 kg/mmol-hr, about 70 kg/mmol-hr, about 80 kg/mmol-hr, about 90 kg/mmol-hr, or about 100 kg/mmol-hr to about 120 kg/mmol-hr, about 150 kg/mmol-hr, about 180 kg/mmol-hr, about 200 kg/mmol-hr, about 250 kg/mmol-hr, about 300 kg/mmol-hr, about 350 kg/mmol-hr, about 400 kg/mmol-hr, about 450 kg/mmol-hr, about 500 kg/mmol-hr, about 550 kg/mmol-hr, about 600 kg/mmol-hr, about 700 kg/mmol-hr, about 800 kg/mmol-hr, about 900 kg/mmol-hr, about 1,000 kg/mmol-hr, about 1,200 kg/mmol-hr, about 1,500 kg/mmol-hr, about 2,000 kg/mmol-hr, or greater. For example, the catalyst system, the transition metal complex, and/or the catalyst has a catalytic activity of about 10 kg/mmol-hr to about 2,000 kg/mmol-hr, about 10 kg/mmol-hr to about 1,500 kg/mmol-hr, about 10 kg/mmol-hr to about 1,000 kg/mmol-hr, about 10 kg/mmol-hr to about 800 kg/mmol-hr, about 10 kg/mmol-hr to about 700 kg/mmol-hr, about 10 kg/mmol-hr to about 600 kg/mmol-hr, about 10 kg/mmol-hr to about 500 kg/mmol-hr, about 10 kg/mmol-hr to about 400 kg/mmol-hr, about 10 kg/mmol-hr to about 300 kg/mmol-hr, about 50 kg/mmol-hr to about 1,500 kg/mmol-hr, about 50 kg/mmol-hr to about 1,000 kg/mmol-hr, about 50 kg/mmol-hr to about 800 kg/mmol-hr, about 50 kg/mmol-hr to about 700 kg/mmol-hr, about 50 kg/mmol-hr to about 600 kg/mmol-hr, about 50 kg/mmol-hr to about 500 kg/mmol-hr, about 50 kg/mmol-hr to about 400 kg/mmol-hr, about 50 kg/mmol-hr to about 300 kg/mmol-hr, about 100 kg/mmol-hr to about 1,500 kg/mmol-hr, about 100 kg/mmol-hr to about 1,000 kg/mmol-hr, about 100 kg/mmol-hr to about 800 kg/mmol-hr, about 100 kg/mmol-hr to about 700 kg/mmol-hr, about 100 kg/mmol-hr to about 600 kg/mmol-hr, about 100 kg/mmol-hr to about 500 kg/mmol-hr, about 100 kg/mmol-hr to about 400 kg/mmol-hr, about 100 kg/mmol-hr to about 300 kg/mmol-hr, about 200 kg/mmol-hr to about 1,500 kg/mmol-hr, about 200 kg/mmol-hr to about 1,000 kg/mmol-hr, about 200 kg/mmol-hr to about 800 kg/mmol-hr, about 200 kg/mmol-hr to about 700 kg/mmol-hr, about 200 kg/mmol-hr to about 600 kg/mmol-hr, about 200 kg/mmol-hr to about 500 kg/mmol-hr, about 200 kg/mmol-hr to about 400 kg/mmol-hr, about 200 kg/mmol-hr to about 300 kg/mmol-hr, about 400 kg/mmol-hr to about 1,500 kg/mmol-hr, about 400 kg/mmol-hr to about 1,000 kg/mmol-hr, about 400 kg/mmol-hr to about 800 kg/mmol-hr, about 400 kg/mmol-hr to about 700 kg/mmol-hr, about 400 kg/mmol-hr to about 600 kg/mmol-hr, about 400 kg/mmol-hr to about 500 kg/mmol-hr, about 400 kg/mmol-hr to about 400 kg/mmol-hr, or about 400 kg/mmol-hr to about 300 kg/mmol-hr.

In one or more examples, the catalyst system, the transition metal complex, and/or the catalyst has a catalytic activity of in a range from about 10 kg/mmol-hr to about 1,000 kg/mmol-hr, about 100 kg/mmol-hr to about 1,000 kg/mmol-hr, about 100 kg/mmol-hr to about 600 kg/mmol-hr, about 200 kg/mmol-hr to about 600 kg/mmol-hr, about 400 kg/mmol-hr to about 600 kg/mmol-hr, or alternatively, about 100 kg/mmol-hr to about 200 kg/mmol-hr.

In one or more embodiments, the conversion of olefin monomer is at least 10%, based upon polymer yield and the weight of the monomer entering the reaction zone, such as 20% or more, such as 30% or more, such as 50% or more, such as 80% or more. In one or more embodiments, a catalyst of the present disclosure has an activity of 150,000 to about 600,000 g/mmol/hour.

In one or more embodiments, a catalyst of the present disclosure, such as a compound of Formulas (II), (V), (VI), and (VII(a)-(l)) is capable of producing a polymer or a copolymer, such as polyethylene or polyethylene-octene, having an Mw of about 30,000, about 50,000, about 70,000, or about 80,000 to about 90,000, about 100,000, about 120,000, about 140,000, about 150,000, about 180,000, about 200,000, about 250,000, about 500,000, or about 1,000,000. For example, the polymer has an Mw in a range from about 30,000 to about 1,000,000, about 50,000 to about 500,000, about 60,000 to about 300,000, or about 80,000 to about 200,000. In another embodiment, a catalyst of the present disclosure is capable of producing a polymer or a copolymer, such as polyethylene or polyethylene-octene, having an Mn of about 20,000, about 25,000, about 30,000, or about 35,000 to about 40,000, about 45,000, about 50,000, about 60,000, about 70,000, about 80,000, about 90,000, about 100,000, about 120,000, or about 150,000. For example, the polymer has an Mn in a range from about 20,000 to about 150,000, about 25,000 to about 120,000, about 30,000 to about 100,000, or about 40,000 to about 100,000. In one or more embodiments, a catalyst of the present disclosure is capable of producing a polymer or a copolymer, such as polyethylene or polyethylene-octene, having an Mw/Mn value from about 1 to about 5, for example, about 1.5 to about 4, about 1.5 to about 3, about 1.5 to about 2.5.

In one or more embodiments, little or no alumoxane is used in the process to produce the polymers. Alumoxane can be present at zero mol %, alternatively the alumoxane is present at a molar ratio of aluminum to transition metal less than 500:1, such as less than 300:1, such as less than 100:1, such as less than 1:1.

In some embodiments, little or no scavenger is used in the process to produce the ethylene polymer. Scavenger (such as trialkyl aluminum) can be present at zero mol %, alternately the scavenger is present at a molar ratio of scavenger metal to transition metal of less than 100:1, such as less than 50:1, such as less than 15:1, such as less than 10:1.

In one or more embodiments, the polymerization: 1) is conducted at temperatures of about 0° C. to about 300° C. (such as about 25° C. to about 150° C., such as about 40° C. to about 120° C., such as about 70° C. to about 110° C.); 2) is conducted at a pressure of atmospheric pressure to 10 MPa (such as about 0.35 MPa to about 10 MPa, such as from about 0.45 MPa to about 6 MPa, such as from about 0.5 MPa to about 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, where aromatics are present in the solvent at less than 1 wt %, such as less than 0.5 wt %, such as at 0 wt % based upon the weight of the solvents); and 4) the activity of the catalyst compound is at least 80,000 g/mmol-hr, such about 150,000 g/mmol-hr, about 200,000 g/mmol-hr, about 250,000 g/mmol-hr, about 300,000 g/mmol-hr, or greater. In one or more embodiments, the catalyst system used in the polymerization includes no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In one or more embodiments, the polymerization occurs in one reaction zone.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Chain Transfer Agent

A "chain transfer agent" (CTA) is any agent capable of hydrocarbyl and/or polymeryl group exchange between a coordinative polymerization catalyst and the metal center of the chain transfer agent during a polymerization process. The chain transfer agent can be any desirable chemical compound such as those disclosed in WO 2007/130306. The chain transfer agent can be selected from Group 2, 12, or 13 alkyl or aryl compounds, such as zinc, magnesium, or aluminum alkyls or aryls. In some examples, the alkyl is a $C_1$-$C_{30}$ alkyl, a $C_2$-$C_{20}$ alkyl, or a $C_3$-$C_{12}$ alkyl. Exemplary alkyls for the CTA can be or include, but are not limited to, methyl, ethyl, propyl, butyl, isobutyl, tertbutyl, pentyl, hexyl, cyclohexyl, phenyl, octyl, nonyl, decyl, undecyl, dodecyl, isomers thereof, or any combination thereof.

In one or more examples, the chain transfer agent is selected from dialkyl zinc compounds, where each alkyl can independently be methyl, ethyl, propyl, butyl, isobutyl, tertbutyl, pentyl, hexyl, cyclohexyl, or phenyl. In some examples, the chain transfer agent is selected from trialkyl aluminum compounds, where each alkyl can independently be methyl, ethyl, propyl, butyl, isobutyl, tertbutyl, pentyl, hexyl, or cyclohexyl. In other examples, the chain transfer agent is selected from tri aryl aluminum compounds where the aryl is selected from phenyl and substituted phenyl.

The chain transfer process may be characterized by the transfer of at least 0.5 polymer chains (e.g., 0.5 to 3) polymer chains, where n is the maximum number of polymer chains that can be transferred to the chain transfer agent metal, such as n is 1 to 3 for trivalent metals (such as Al) and 1 to 2 for divalent metals (such as Zn), such as n is 1.5 to 3 for trivalent metals (such as Al) and 1.5 to 2 for divalent metals (such as Zn). The number of chains transferred per metal is the slope of the plot of moles of polymer produced versus the moles of the chain transfer agent metal (as determined from at least four points, CTA metal:catalyst transition metal of 20:1, 80:1, 140:1 and 200:1, using least squares fit (Microsoft™ Excel 2010, version 14.0.7113.5000 (32 bit)) to draw the line.

Useful chain transfer agents are typically present at from 10 or 20 or 50 or 100 equivalents to 600 or 700 or 800 or 1,000 or 2,000 or 4,000 equivalents relative to the catalyst component. Alternately the chain transfer agent is preset at a catalyst complex-to-CTA molar ratio of from about 1:12,000 to 10:1; alternatively 1:6,000; alternatively, 1:3,000 to 10:1; alternatively 1:2,000 to 10:1; alternatively 1:1,000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1.

Exemplary chain transfer agents can be or include a compound represented by the formula $AlR_3$, $MgR_2$, or $ZnR_2$, where each R is, independently, a $C_1$-$C_8$ hydrocarbyl, such as methyl, ethyl, propyl, butyl, phenyl, hexyl, octyl, or an isomer thereof. Exemplary chain transfer agents can be or include, but are not limited to, diethylzinc, tri-n-octyl aluminum, trimethylaluminum, triethylaluminum, tri-isobutylaluminum, tri-n-hexylaluminum, trioctylaluminum, diethyl aluminum chloride, methyl alumoxane, dibutyl zinc, di-n-propylzinc, di-n-hexylzinc, di-n-pentylzinc, di-n-decylzinc, di-n-dodecylzinc, di-n-tetradecylzinc, di-n-hexadecylzinc, di-n-octadecylzinc, diphenylzinc, diisobutylaluminum hydride, diethylaluminum hydride, di-n-octylaluminum hydride, dibutylmagnesium, diethylmagnesium, dihexylmagnesium, triethylboron, or any combination thereof.

In other embodiments, two or more complexes are combined with diethyl zinc and/or tri-n-octylaluminum in the same reactor with monomer(s). Alternately, one or more complexes is/are combined with another catalyst and diethyl zinc and/or tri-n-octylaluminum in the same reactor with monomers.

In some embodiments, one or more complexes is/are combined with a mixture of diethyl zinc and an aluminum reagent in the same reactor with monomer(s). Alternately, one or more complexes is/are combined with two chain transfer agents in the same reactor with monomers.

Polyolefin Products

The present disclosure also provides compositions of matter which can be produced by the methods described herein.

In one or more embodiments, the process described herein produces ethylene homopolymers or ethylene copolymers, such as propylene-ethylene and/or ethylene-alphaolefin (such as $C_4$ to $C_{20}$) copolymers (such as ethylene-hexene copolymers or ethylene-octene copolymers) having an Mw/Mn of greater than 1 to 4 (such as greater than 1 to 3).

Likewise, the process of the present disclosure produces olefin polymers, such as polyethylene and polypropylene homopolymers and copolymers. In one or more embodiments, the polymers produced herein are homopolymers of ethylene or propylene, are copolymers of ethylene such as copolymer of ethylene having from 0 mol % to about 25 mol % (such as from about 0.5 mol % to about 20 mol %, such as from about 1 mol % to about 15 mol %, such as from about 3 mol % to about 10 mol %) of one or more $C_3$ to $C_{20}$ olefin comonomer (such as $C_3$ to $C_{12}$ alpha-olefin, such as propylene, butene, hexene, octene, decene, dodecene, such as propylene, butene, hexene, octene), or are copolymers of propylene such as copolymers of propylene having from 0 mol % to about 25 mol % (such as from about 0.5 mol % to about 20 mol %, such as from about 1 mol % to about 15 mol %, such as from about 3 mol % to about 10 mol %) of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In one or more embodiments, the monomer is ethylene and the comonomer is hexane or octene, such as from about 1 wt % to about 15 wt % of hexane or octene, for example, about 1 wt % to about 10 wt % of hexane or octene or about 2 wt % to about 8 wt % of hexane or octene.

In one or more embodiments, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

In one or more embodiments, a bimodal polymer, such as a bimodal polyethylene (e.g., formed by a catalyst system having a catalyst represented by Formulas (II), (V), (VI), and (VII(a)-(l)) and another type of catalyst, such as, for example, a metallocene catalyst) has an Mw/Mn value from about 1 to about 10, for example, about 1.5 to about 8, about 2 to about 4, or about 2 to about 3.

In one or more embodiments, the polymer produced herein has a composition distribution breadth index (CDBI) of 50% or more, such as 60% or more, such as 70% or more. CDBI is a measure of the composition distribution of monomer within the polymer chains and is measured by the procedure described in PCT publication WO 1993/003093, published Feb. 18, 1993, specifically columns 7 and 8 as well as in Wild et al., *J. Poly. Sci., Poly. Phys. Ed.*, v. 20, p. 441 (1982) and U.S. Pat. No. 5,008,204, including that fractions having a weight average molecular weight (Mw) below 15,000 are ignored when determining CDBI.

Blends

In one or more embodiments, the polymer (such as polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, LDPE, LLDPE, HDPE, random copolymer of ethylene and propylene, and/or butene, hexene, polybutene, ethylene vinyl acetate, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In one or more embodiments, the polymer (such as polyethylene or polypropylene) is present in the above blends, at from 10 to 99 wt %, based upon the weight of the polymers in the blend, such as 20 to 95 wt %, such as at least 30 to 90 wt %, such as at least 40 to 90 wt %, such as at least 50 to 90 wt %, such as at least 60 to 90 wt %, such as at least 70 to 90 wt %.

The blends described above may be produced by mixing the polymers of the present disclosure with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; and talc.

Films

Specifically, any of the foregoing polymers, such as the foregoing polyethylenes or blends thereof, may be used in a variety of end-use applications. Such applications include, for example, mono- or multi-layer blown, extruded, and/or shrink films. These films may be formed by any number of extrusion or coextrusion techniques, such as a blown bubble film processing technique, wherein the composition can be extruded in a molten state through an annular die and then expanded to form a uniaxial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, such as between 5 and 7, and in the Transverse Direction (TD) at a ratio of up to 15, such as 7 to 9. However, in at least one embodiment the film is oriented to the same extent in both the MD and TD directions.

The films may vary in thickness depending on the intended application; however, films of a thickness from about 1 μm to about 50 μm are usually suitable. Films intended for packaging are usually from about 10 μm to about 50 μm thick. The thickness of the sealing layer is typically about 0.2 μm to about 50 μm. There may be a sealing layer on both the inner and outer surfaces of the film or the sealing layer may be present on only the inner or the outer surface.

In one or more embodiments, one or more layers may be modified by corona treatment, electron beam irradiation, gamma irradiation, flame treatment, or microwave. In one or more embodiments, one or both of the surface layers is modified by corona treatment.

This invention further relates to:
1. A ligand represented by Formula (I):

$$\text{(I)}$$

wherein:
each Q is independently a Group 15 atom or a Group 16 atom,
each n is independently 0 or 1, wherein n is 0 if Q is a Group 16 atom or n is 1 if Q is a Group 15 atom;
$L^1$ is and is not part of an aromatic ring;
$L^2$ is and is not part of an aromatic ring, wherein y is an integer of 2, 3, 4, 5, 6, 7, 8, 9, or 10;

$R^1$ is a substituted or unsubstituted linear, branched, cyclic, polycyclic, heterocyclic, or aromatic $C_1$-$C_{18}$ diyl;

each $R^2$ is independently a hydrogen, a halogen, a substituted or unsubstituted $C_1$-$C_{40}$ hydrocarbyl, or a heteroatom-containing group; or two or more adjacent $R^2$ groups are joined together to form a $C_4$-$C_{62}$ cyclic, polycyclic, or heterocyclic group that is not aromatic;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

2. A transition metal complex represented by Formula (II):

$$\text{(II)}$$

wherein:
M is a Group 4 transition metal;
each Q is independently a Group 15 atom or a Group 16 atom;
each n is independently 0 or 1, wherein n is 0 if Q is a Group 16 atom or n is 1 if Q is a Group 15 atom;
$L^1$ is and is not part of an aromatic ring;
$L^2$ is and is not part of an aromatic ring, wherein y is an integer of 2, 3, 4, 5, 6, 7, 8, 9, or 10;

each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;

$R^1$ is a substituted or unsubstituted linear, branched, cyclic, polycyclic, heterocyclic, or aromatic $C_1$-$C_{18}$ diyl;

each $R^2$ is independently a hydrogen, a halogen, a substituted or unsubstituted $C_1$-$C_{40}$ hydrocarbyl, or a heteroatom-containing group; or two or more adjacent $R^2$ groups are joined together to form a $C_4$-$C_{62}$ cyclic, polycyclic, or heterocyclic group that is not aromatic;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

3. The transition metal complex of paragraph 2, wherein M is Hf or Zr.

4. The ligand or the transition metal complex according to any one of paragraphs 1-3, wherein Q is O, N, S, or P.

5. The ligand or the transition metal complex of paragraph 4, wherein Q is N, and wherein each $R^3$ is independently a hydrogen or a substituted or unsubstituted $C_1$-$C_{10}$ hydrocarbyl.

6. The ligand or the transition metal complex according to any one of paragraphs 1-5, wherein each $R^2$ is independently a hydrogen or a substituted or unsubstituted $C_1$-$C_{10}$ hydrocarbyl.

7. The ligand or the transition metal complex of paragraph 6, wherein each $R^2$ is independently a hydrogen or a substituted or unsubstituted $C_1$-$C_5$ hydrocarbyl, and wherein y is an integer of 2, 3, 4, or 5.

8. The ligand or the transition metal complex of paragraph 7, wherein each $R^2$ on $L^1$ and $L^2$ is independently a hydrogen or a substituted or unsubstituted $C_1$-$C_3$ hydrocarbyl, and wherein y is an integer of 2 or 3.

9. The ligand or the transition metal complex according to any one of paragraphs 1-8, wherein $L^1$ is an unsubstituted methanediyl and $L^2$ is an unsubstituted ethanediyl.

10. The transition metal complex according to any one of paragraphs 2-9, wherein each $X^1$ and $X^2$ is independently a substituted or unsubstituted $C_1$-$C_{20}$ hydrocarbyl.

11. The transition metal complex according to any one of paragraphs 2-10, wherein each $X^1$ and $X^2$ is independently a substituted or unsubstituted $C_1$-$C_8$ alkyl, a phenyl, a benzyl, a cyclohexyl, or halide-substituted analogues thereof.

12. The transition metal complex according to any one of paragraphs 2-11, wherein each $X^1$ and $X^2$ is independently a halide.

13. The ligand or the transition metal complex according to any one of paragraphs 1-12, wherein $R^1$ is a substituted or unsubstituted linear, branched, cyclic, polycyclic, heterocyclic, or aromatic $C_1$-$C_{10}$ diyl.

14. The ligand or the transition metal complex of paragraph 13, wherein $R^1$ is a substituted or unsubstituted linear or branched $C_1$-$C_6$ diyl.

15. The ligand or the transition metal complex of paragraph 14, wherein $R^1$ is an unsubstituted ethanediyl.

16. The ligand or the transition metal complex according to any one of paragraphs 1-15, wherein each $R^4$ and $R^8$ is independently halogen, carbazolyl, fluorenyl, adamantly, indolyl, indolinyl, imidazolyl, indenyl, indanyl, or substitutes thereof.

17. The ligand or the transition metal complex of paragraph 16, wherein $R^4$ is carbazolyl, fluorenyl, adamantly, or substitutes thereof, and $R^8$ is halogen.

18. The ligand or the transition metal complex according to any one of paragraphs 1-17, wherein each $R^5$, $R^6$, $R^7$, $R^9$, $R^{10}$, and $R^{11}$ is independently a hydrogen or a substituted or unsubstituted linear or branched $C_1$-$C_{10}$ hydrocarbyl.

19. The ligand or the transition metal complex of paragraph 18, wherein each $R^5$, $R^7$, $R^9$, and $R^{11}$ is a hydrogen and each $R^6$ and $R^{10}$ is a substituted or unsubstituted linear or branched $C_1$-$C_4$ hydrocarbyl.

20. A catalyst system comprising an activator and the transition metal complex according to any one of paragraphs 2-19.

21. The catalyst system of paragraph 20, wherein the catalyst system further comprises a chain transfer agent.

22. The catalyst system of paragraph 21, wherein the chain transfer agent comprises a $C_1$-$C_{20}$ alkyl aluminum compound, a $C_1$-$C_{20}$ alkyl zinc compound, or a combination thereof.

23. The catalyst system of paragraph 22, wherein the chain transfer agent comprises a $C_1$-$C_5$ alkyl aluminum compound, a $C_1$-$C_5$ alkyl zinc compound, or a combination thereof.

24. The catalyst system according to any one of paragraphs 21-23, wherein the chain transfer agent is present in the catalyst system at a molar ratio of the transition metal to the chain transfer agent of 10:1 or greater.

25. The catalyst system according to any one of paragraphs 20-24, wherein the activator is an alumoxane.

26. The catalyst system according to any one of paragraphs 20-25, wherein the activator is a non-coordinating anion.

27. The catalyst system according to any one of paragraphs 20-26, wherein the activator is selected from the group consisting of methyl alumoxane, ethyl alumoxane, isobutyl alumoxane, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetra(perfluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, and any combination thereof.

28. The catalyst system according to any one of paragraphs 20-27, further comprising a support material.

29. A polymerization process to produce polyolefin, comprising:
   contacting olefin monomers with the catalyst system of any one of paragraphs 20-28; and
   recovering olefin polymer.

30. The polymerization process of paragraph 29, wherein the olefin monomers comprise ethylene, propylene, or a combination thereof.

31. The polymerization process of paragraphs 29 or 30, wherein the catalyst system or the transition metal complex has a catalytic activity in a range from about 10 kg/mmol-hr to about 1,000 kg/mmol-hr.

32. The polymerization process of paragraph 29 or 30, wherein the catalytic activity is in a range from about 100 kg/mmol-hr to about 1,000 kg/mmol-hr.

33. The polymerization process of paragraph 29 or 30, wherein the catalytic activity is in a range from about 100 kg/mmol-hr to about 600 kg/mmol-hr.

34. The polymerization process of paragraph 29 or 30, wherein the catalytic activity is in a range from about 200 kg/mmol-hr to about 600 kg/mmol-hr.

35. The polymerization process of paragraph 29 or 30, wherein the catalytic activity is in a range from about 400 kg/mmol-hr to about 600 kg/mmol-hr.

36. A transition metal complex represented by Formula (V):

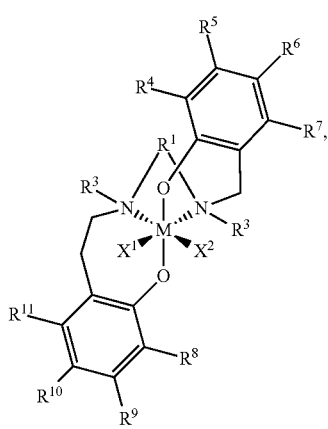

(V)

wherein:

M is a Group 4 transition metal;

each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;

$R^1$ is a substituted or unsubstituted linear, branched, cyclic, polycyclic, heterocyclic, or aromatic $C_1$-$C_{18}$ diyl;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, heterocyclic, or aromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

37. A transition metal complex represented by Formula (VI):

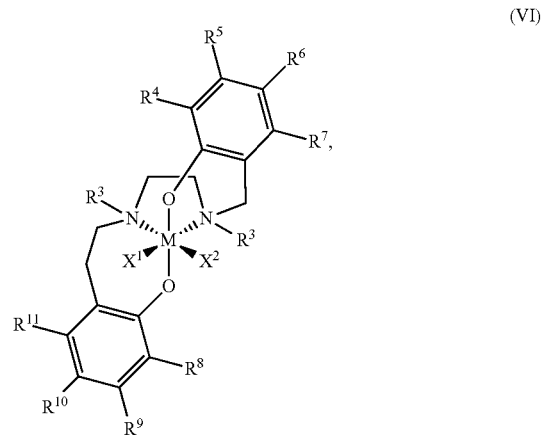

(VI)

wherein:

M is Ti, Zr, or Hf;

each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

38. A transition metal complex represented by Formula (VII(a)):

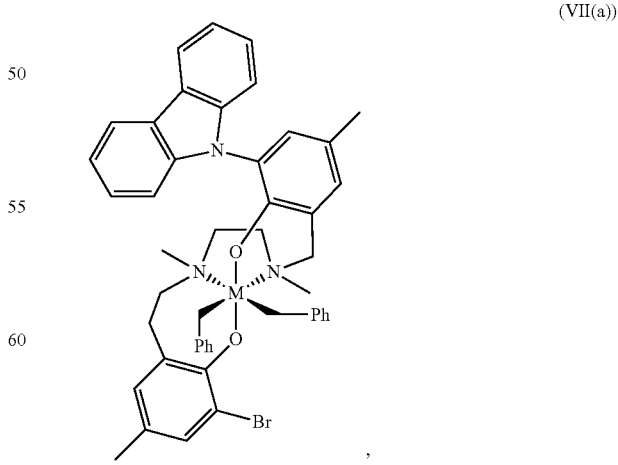

(VII(a))

wherein M is Ti, Zr, or Hf.

39. A ligand represented by Formula (IV(a)):

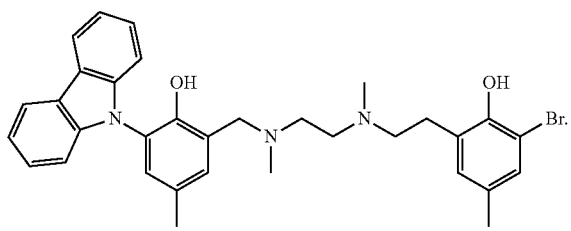

EXPERIMENTAL $^1$H NMR for Ligand and Catalyst Characterization: Chemical structures are determined by 1H NMR. 1H NMR data are collected at room temperature (e.g., 23° C.) in a 5 mm probe using either a 400 or 500 MHz Bruker spectrometer with deuterated methylene chloride or deuterated benzene.

EXAMPLES

Synthesis of Catalysts (and Catalyst Precursor Compounds)

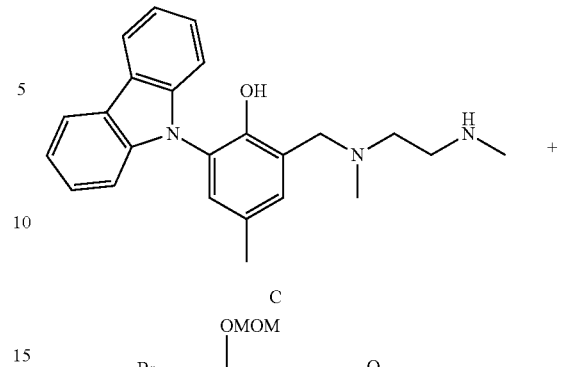

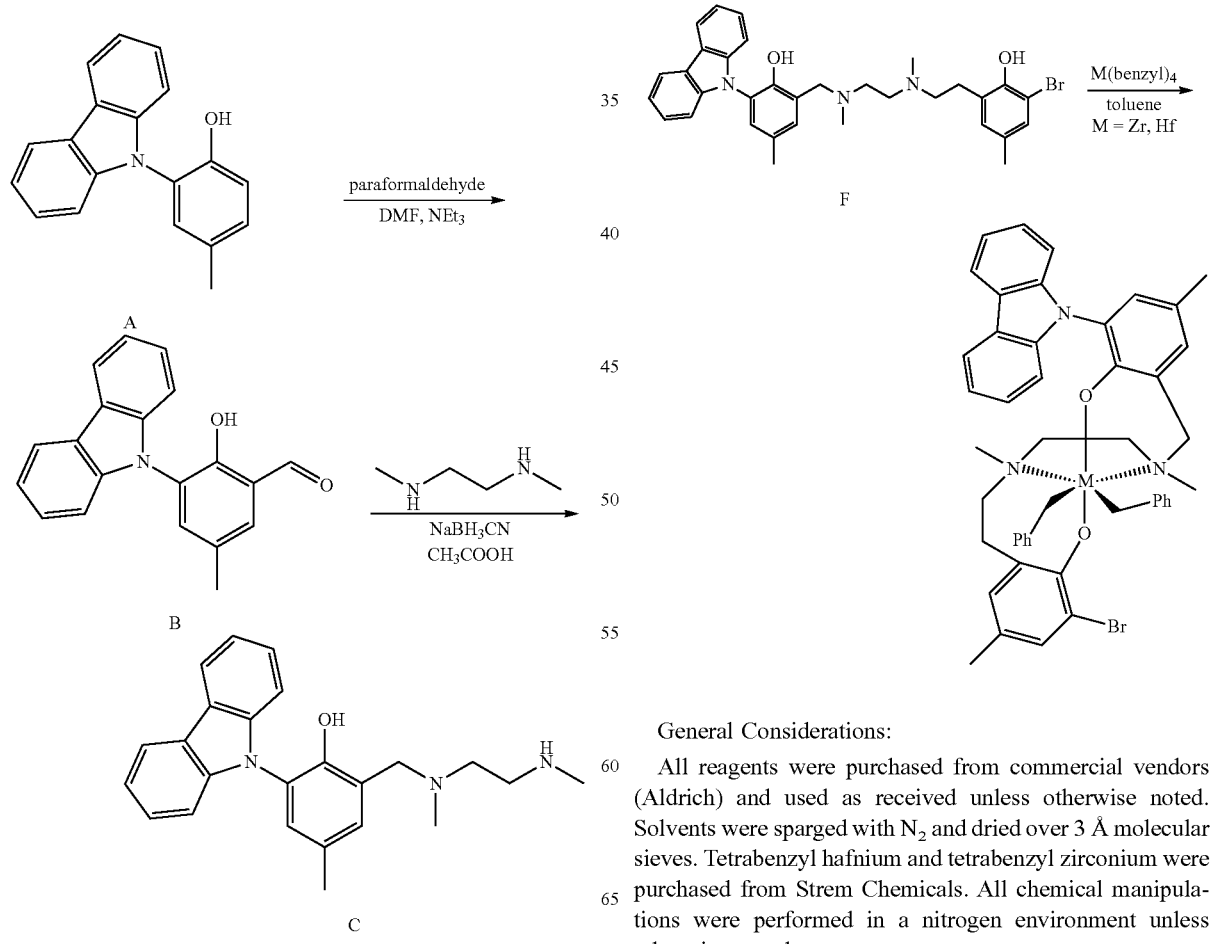

General Considerations:

All reagents were purchased from commercial vendors (Aldrich) and used as received unless otherwise noted. Solvents were sparged with $N_2$ and dried over 3 Å molecular sieves. Tetrabenzyl hafnium and tetrabenzyl zirconium were purchased from Strem Chemicals. All chemical manipulations were performed in a nitrogen environment unless otherwise stated.

3-(9H-carbazol-9-yl)-2-hydroxy-5-methylbenzaldehyde (B)

2-(carbazolyl)-4-methylphenol (9.65 mmol), magnesium dichloride (2.5 equiv.), trimethylamine (3.0 equiv.), and paraformaldehyde (6 equiv.) were slurried in 150 mL of acetonitrile. The slurry was stirred at room temperature (about 23° C.) for about 2 hours during which the slurry turned bright yellow in color. The reaction flask was then cooled to −35° C. and DMF (5 equiv.) was slowly added. The reaction was allowed to warm to room temperature and stirred overnight. The resulting mixture was poured into 250 mL of 1M HCl and extracted with ethyl acetate. The organic layer was washed with brine, dried with $MgSO_4$, filtered, and concentrated. The residue was purified on a Biotage SNAP Ultra column with a solvent gradient of 0-20% ethyl acetate/hexane.

2-(9H-carbazol-9-yl)-4-methyl-6-((methyl(2-(methylamino)ethyl)amino)methyl)phenol (C)

A 100 mL round-bottom flask was charged with aldehyde B (2 equivalents), $N^1,N^2$-dimethylethane-1,2-diamine (5 equivalents) and 40 mL of methanol and the resulting mixture was stirred. Sodium cyanoborohydride and acetic acid were added to the flask and mixture was further stirred at room temperature overnight. The solvent was removed and the residue was dissolved in 50 mL of dichloromethane. The resulting solution was washed with water (2×50 mL), dried with $MgSO_4$, filtered, and concentrated. The crude product was loaded onto a Biotage sample cartridge and purified using a solvent gradient of 5-20% ethyl acetate in hexane to obtain compound C.

2-(((2-((3-bromo-2-(methoxymethoxy)-5-methylphenethyl)(methyl)amino)ethyl)(methyl) amino)methyl)-6-(9H-carbazol-9-yl)-4-methylphenol (E)

A 100 mL round-bottom flask was charged C (1 equivalent), D (1 equivalent) and 40 mL of methanol and the resulting mixture was stirred at room temperature. Sodium cyanoborohydride and acetic acid were added to the flask and the reaction was further stirred overnight. The volatiles were then removed and the residue was dissolved in 50 mL of dichloromethane. The mixture was washed with water (2×50 mL), dried with $MgSO_4$, filtered and concentrated. The crude product was loaded onto a Biotage sample cartridge and purified using a solvent gradient of 5-20% ethyl acetate in hexane to obtain compound E.

2-(2-((2-((3-(9H-carbazol-9-yl)-2-hydroxy-5-methylbenzyl)(methyl)amino)ethyl)(methyl) amino)ethyl)-6-bromo-4-methylphenol (F)

In a 50 mL round-bottom flask, compound E was dissolved in about 20 mL of tetrahydrofuran. Hydrochloric acid (10 equiv.) in THF was added and the reaction was stirred overnight. Solid sodium bicarbonate was added to basify the solution, then extracted with ethyl acetate (30 mL). The organic portion was washed with water (2×30 mL), dried with $MgSO_4$, filtered, and concentrated. The residue was purified using a Biotage Ultra silica column with a solvent gradient of 5-40% ethyl acetate in hexane to obtain pure F.

Metallation:
In a nitrogen atmosphere, the ligand F was dissolved in 4 mL of toluene in a 20 mL vial. Tetrabenzyl zirconium or hafnium was dissolved in 4 mL of toluene in a separate vial. The solutions were combined and stirred at room temperature for one hour then filtered through a 0.2 μm syringe filter and concentrated. The residue was washed with pentane and dried under vacuum.

POLYMERIZATION EXAMPLES

General Polymerization Procedures for Parallel Pressure Reactor.

Solvents, polymerization-grade toluene, and isohexane were supplied by ExxonMobil Chemical Company and purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (C8) and 1-hexene (C6) (98%, Aldrich Chemical Company) were dried by stirring over NaK overnight followed by filtration through basic alumina (Aldrich Chemical Company, Brockman Basic 1).

Polymerization-grade ethylene ($C_2$) was used and further purified by passing the gas through a series of columns: 500 cc Oxyclear cylinder from Labclear (Oakland, Calif.) followed by a 500 cc column packed with dried 3 Å mole sieves (8-12 mesh; Aldrich Chemical Company) and a 500 cc column packed with dried 5 Å mole sieves (8-12 mesh; Aldrich Chemical Company).

Polymerization grade propylene ($C_3$) was used and further purified by passing it through a series of columns: 2,250 cc Oxiclear cylinder from Labclear followed by a 2,250 cc column packed with 3 Å mole sieves (8-12 mesh; Aldrich Chemical Company), then two 500 cc columns in series packed with 5 Å mole sieves (8-12 mesh; Aldrich Chemical Company), then a 500 cc column packed with Selexsorb CD (BASF), and finally a 500 cc column packed with Selexsorb COS (BASF).

Solutions of the metal complexes and activators were prepared in a drybox using toluene (ExxonMobil Chemical Company; anhydrous, stored under nitrogen; 98%). Concentrations were typically 0.2 mmol/L for the metal complexes and N,N-dimethyl anilinium tetrakis-pentafluorophenyl borate (Activator 1 or A1) or 0.5% w/w for methyl alumoxane (MAO).

Slurries of supported catalysts in toluene were prepared in the drybox using 45 mg of the supported catalyst and 15 mL of toluene. The resulting mixture was vortexed for uniform distribution of particles prior to injection.

For polymerization experiments with supported catalysts or D4-DMAH as activator, tri-n-octylaluminum (TNOAL, neat, AkzoNobel) was used as a scavenger. Concentration of the TNOAL solution in toluene ranged from 0.5 to 2.0 mmol/L.

Polymerizations were carried out in a parallel, pressure reactor, as generally described in U.S. Pat. Nos. 6,306,658; 6,455,316; 6,489,168; WO 2000/009255; and Murphy et al., *J. Am. Chem. Soc.*, 2003, v. 125, pp. 4306-4317, each of which is fully incorporated herein by reference. The experiments were conducted in an inert atmosphere ($N_2$) drybox using autoclaves equipped with an external heater for temperature control, glass inserts (internal volume of reactor=23.5 mL for $C_2$ and $C_2/C_8$; 22.5 mL for $C_3$ runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25°

C. for 5 hours. Although the specific quantities, temperatures, solvents, reactants, reactant ratios, pressures, and other variables are frequently changed from one polymerization run to the next, the following describes a typical polymerization performed in a parallel, pressure reactor.

Catalyst systems dissolved in solution were used in the polymerization examples below, unless specified otherwise.

Ethylene Homopolymerization (HDPE) and Ethylene-Octene Copolymerization (EO).

A pre-weighed glass vial insert and disposable stirring paddle were fitted to each reaction vessel of the reactor, which contains 48 individual reaction vessels. The reactor was then closed and purged with ethylene. Each vessel was charged with enough solvent (typically isohexane) to bring the total reaction volume, including the subsequent additions, to the desired volume, typically 5 mL. 1-octene, if required, was injected into the reaction vessel and the reactor was heated to the set temperature and pressurized to the predetermined pressure of ethylene, while stirring at 800 rpm. The aluminum and/or zinc compound in toluene was then injected as scavenger and/or chain transfer agent followed by addition of the activator solution (typically 1.0-1.2 molar equivalents of N,N-dimethyl anilinium tetrakis-pentafluorophenyl borate—Activator 1).

The catalyst solution (typically 0.020-0.080 µmol of metal complex) was injected into the reaction vessel and the polymerization was allowed to proceed until a pre-determined amount of ethylene (quench value is about 20 psi) had been used up by the reaction. Alternatively, the reaction may be allowed to proceed for a set amount of time (maximum reaction time is about 30 minutes). Ethylene was added continuously (through the use of computer controlled solenoid valves) to the autoclaves during polymerization to maintain reactor gauge pressure (+/−2 psig) and the reactor temperature was monitored and typically maintained within +/−1° C. The reaction was quenched by pressurizing the vessel with compressed air. After the reactor was vented and cooled, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent octene incorporation, and by DSC (see below) to determine melting point (Tm).

For polymerizations using MAO as activator (typically about 100 to 1,000 molar equivalents), the MAO solution was injected into the reaction vessel after the addition of 1-octene and prior to heating the vessel to the set temperature and pressurizing with ethylene. No additional aluminum reagent was used as scavenger during these runs.

Equivalence is determined based on the mole equivalents relative to the moles of the transition metal in the catalyst complex.

Ethylene-Propylene Copolymerization (EP).

The reactor was prepared as described above and purged with propylene. Isohexane was then injected into each vessel at room temperature followed by a predetermined amount of propylene gas. The reactor was heated to the set temperature and pressurized with the required amount of ethylene while stirring at 800 rpm. The scavenger, activator (typically D4-DMAH) and catalyst solutions were injected sequentially to each vessel and the polymerization was allowed to proceed as described previously.

Propylene Homopolymerization (PP).

The reactor was prepared as described above and purged with propylene. Isohexane was then injected into each vessel at room temperature followed by a predetermined amount of propylene gas. The reactor was heated to the set temperature while stirring at 800 rpm, and the scavenger, activator (typically D4-DMAH) and catalyst solutions were injected sequentially to each vessel. The polymerization was allowed to proceed as described previously.

For propylene homopolymerization in the presence of hydrogen (PP/$H_2$), the reactor was prepared as described above and purged with 25% v/v $H_2/N_2$ gas. With an atmosphere of $H_2/N_2$ gas in the reaction vessel, isohexane, the scavenger solution and a predetermined amount of propylene gas were injected sequentially at room temperature. The reactor was then heated to the set temperature followed by sequential injection of the activator and catalyst solutions. The polymerization was allowed to proceed as described previously.

For polymerizations using MAO as activator, the MAO solution was injected into the vessel after the addition of isohexane. No additional aluminum reagent was used as scavenger during these runs.

Polymer Characterization.

Polymer sample solutions were prepared by dissolving polymer in 1,2,4-trichlorobenzene (TCB, 99+% purity from Sigma-Aldrich) containing 2,6-di-tertbutyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a 30 series of three 30 cm×7.5 mm linear columns, each containing PLgel 10 µm, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 µL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC) measurements were performed on a TAQ100 instrument to determine the melting point (Tm) of the polymers. Samples were preannealed at 220° C. for 15 minutes and then allowed to cool to room temperature overnight. The samples were then heated to 220° C. at a rate of 100° C./min and then cooled at a rate of 50° C./min. Melting points were collected during the heating period.

The weight percent of ethylene incorporated in polymers was determined by rapid FTIR spectroscopy on a Bruker Equinox 55+IR in reflection mode. Samples were prepared in a thin film format by evaporative deposition techniques. FT-IR methods were calibrated using a set of samples with a range of known wt % ethylene content. For ethylene-1-octene copolymers, the wt % octene in the copolymer was determined via measurement of the methyl deformation band at about 1,375 cm$^{-1}$. The peak height of this band was normalized by the combination and overtone band at about 4,321 cm$^{-1}$, which corrects for path length differences.

For ethylene-propylene copolymers, the wt % ethylene is determined via measurement of the methylene rocking band (about 770 cm$^{-1}$ to about 700 cm$^{-1}$). The peak area of this band is normalized by sum of the band areas of the combination and overtone bands in the range of about 4,500 cm$^{-1}$ to about 4,000 cm$^{-1}$. For samples with composition outside the calibration range, the wt % ethylene was determined by $^1$H NMR spectroscopy or estimated from the polymer Tm.

$^1$H NMR data were collected at 120° C. in a 5 mm probe using a spectrometer with a $^1$H frequency of 500 MHz. Data was recorded using a maximum pulse width of 45°, 5 seconds between pulses and signal averaging 120 transients. Spectral signals were integrated.

Samples were dissolved in deuterated 1,1,2,2,-tetrachloroethane at concentrations of 1-2 wt % prior to being inserted into the spectrometer magnet. Prior to data analysis, spectra were referenced by setting the residual hydrogen-containing solvent resonance to 5.98 ppm. Vinylenes were measured as the number of vinylenes per 1,000 carbon atoms using the resonances between 5.5-5.31 ppm. Trisubstituted end-groups ("trisubs") were measured as the number of trisubstituted groups per 1,000 carbon atoms using the resonances between 5.3-4.85 ppm, by difference from vinyls. Vinyl end-groups were measured as the number of vinyls per 1,000 carbon atoms using the resonances between 5.9-5.65 and between 5.3-4.85 ppm. Vinylidene end-groups were measured as the number of vinylidenes per 1,000 carbon atoms using the resonances between 4.85-4.65 ppm.

Table 1 provides the reaction conditions for ethylene homopolymerization (HDPE) and ethyleneoctene copolymerization (EO) using Activator 1 or MAO.

TABLE 1

| | |
|---|---|
| Catalyst loading | 0.020-0.080 μmol |
| D4-DMAH | 1.1 equiv |
| MAO | 500 equiv |
| Temperature | 80° C. or 100° C. |
| Pressure Setpoint | 95 psi or 135 psi |
| 1-octene | 100 μL |

TABLE 1-continued

| | |
|---|---|
| Total Volume | 5 mL |
| Aluminum compound (scavenger) | 0.5 μmol tri-n-octyl aluminum (TNOAL) |

Table 2 provides catalyst activity and polymer properties for ethylene homopolymerization (HDPE) and ethylene-octene copolymerization (EO) using Activator 1 or MAO. Experiments 1-11 utilized the catalyst represented by Formula (VII(a)) containing zirconium (Zr-VIIa catalyst) and Experiments 12-21 utilized the catalyst represented by Formula (VII(a)) containing hafnium (Hf-VIIa catalyst). Experiments 1-5 and 12-15 included the scavenger TNOAL at a concentration of 0.5 μmol, while the remainder experiments did not contain a scavenger. The catalytic activities in Experiments 1-5 were in a range from about 100-174 kg/mmol-hr, with the exception of Exp. 2 that had a catalytic activity of about 16 kg/mmol-hr. Surprising and unexpected, the catalytic activities in Experiments 6-11 were in a range from about 460-563 kg/mmol-hr, which were the greatest values in the present experiments. The catalytic activities in Experiments 12-21 were less than 100 kg/mmol-hr, such as in a range from about 9-53 kg/mmol-hr.

For comparing catalytic activity, the Zr-VIIa catalyst outperformed the Hf-VIIa catalyst throughout all but one of these experiments. For Experiments 6-11, the Zr-VIIa catalyst at a low concentration (0.02 μmol) and in the presence of the activator MAO and no scavenger achieved the greatest catalytic activities of 563, 527, 481, 504, 460, and 470 kg/mmol-hr, respectively.

TABLE 2

| Catalyst Formula (VII(a)) Zr, Hf | Catalyst Amount (μmol) | Activator | TNOA1 Concn. (μmol) | T (° C.) | P Setpt (psi) | Rxn Time (s) | Yield (g) | Activity (kg/mmol-hr) | Mw (kg/mol) | Mn (kg/mol) | Mw/Mn | wt % C8 = | Tm (° C.) | DHf (J/g) |
|---|---|---|---|---|---|---|---|---|---|---|---|---|---|---|
| Zr | 0.02 | A1 | 0.5 | 80 | 95 | 89 | 0.049 | 100 | 102 | 55 | 1.8 | 7.8 | 125.1 | 136.1 |
| Zr | 0.02 | A1 | 0.5 | 80 | 95 | 422 | 0.037 | 16 | 97 | 52 | 1.9 | 5.6 | 126.6 | 143.8 |
| Zr | 0.02 | A1 | 0.5 | 80 | 95 | 61 | 0.049 | 145 | 89 | 43 | 2.1 | 5.9 | 124.6 | 144.7 |
| Zr | 0.8 | A1 | 0.5 | 100 | 135 | 19 | 0.074 | 174 | 90 | 46 | 1.9 | 4.7 | 126.2 | 148.7 |
| Zr | 0.8 | A1 | 0.5 | 100 | 135 | 23 | 0.079 | 154 | 96 | 55 | 1.7 | 4.3 | 126.2 | 154.3 |
| Zr | 0.02 | MAO | 0 | 80 | 95 | 31 | 0.096 | 563 | 116 | 45 | 2.6 | 7.5 | 122.9 | 125.0 |
| Zr | 0.02 | MAO | 0 | 80 | 95 | 29 | 0.086 | 527 | 95 | 44 | 2.1 | 6.1 | 123.3 | 131.2 |
| Zr | 0.02 | MAO | 0 | 80 | 95 | 30 | 0.081 | 481 | 83 | 31 | 2.6 | 6.4 | 122.0 | 129.4 |
| Zr | 0.02 | MAO | 0 | 100 | 135 | 27 | 0.075 | 504 | 104 | 43 | 2.4 | 6.4 | 123.6 | 137.0 |
| Zr | 0.02 | MAO | 0 | 100 | 135 | 27 | 0.069 | 460 | 82 | 32 | 2.6 | 5.4 | 122.9 | 135.2 |
| Zr | 0.02 | MAO | 0 | 100 | 135 | 27 | 0.070 | 470 | 99 | 42 | 2.4 | 5.2 | 123.0 | 135.9 |
| Hf | 0.08 | A1 | 0.5 | 80 | 95 | 184 | 0.042 | 10 | 116 | 67 | 1.7 | 5.5 | 125.6 | 136.8 |
| Hf | 0.08 | A1 | 0.5 | 80 | 95 | 174 | 0.036 | 9 | 111 | 60 | 1.9 | 4.9 | 126.7 | 144.8 |
| Hf | 0.08 | A1 | 0.5 | 100 | 135 | 147 | 0.045 | 14 | 118 | 71 | 1.7 | 6.8 | 126.4 | 137.1 |
| Hf | 0.08 | A1 | 0.5 | 100 | 135 | 139 | 0.044 | 14 | 107 | 65 | 1.6 | 4.2 | 126.7 | 144.4 |
| Hf | 0.02 | MAO | 0 | 80 | 95 | 182 | 0.053 | 53 | 116 | 53 | 2.2 | 7.7 | 121.0 | 113.3 |
| Hf | 0.02 | MAO | 0 | 80 | 95 | 190 | 0.051 | 48 | 129 | 51 | 2.5 | 7.8 | 120.8 | 115.1 |
| Hf | 0.02 | MAO | 0 | 80 | 95 | 190 | 0.049 | 46 | 124 | 54 | 2.3 | 6.0 | 121.4 | 114.0 |
| Hf | 0.02 | MAO | 0 | 100 | 135 | 158 | 0.044 | 50 | 173 | 70 | 2.5 | 5.6 | 121.0 | 113.0 |
| Hf | 0.02 | MAO | 0 | 100 | 135 | 157 | 0.041 | 47 | 164 | 79 | 2.1 | 6.0 | 121.2 | 115.6 |
| Hf | 0.02 | MAO | 0 | 100 | 135 | 185 | 0.042 | 41 | 199 | 94 | 2.1 | 5.5 | 121.5 | 121.4 |

Overall, novel asymmetric bridged phenolate catalysts, catalyst systems, and methods of the present disclosure are provided. Catalysts, catalyst systems, and methods can provide catalytic activity values of greater than 100 kg/mmol-hr, such as greater than 400 kg/mmol-hr or greater than 500 kg/mmol-hr.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below.

What is claimed is:

1. A transition metal complex represented by Formula (II):

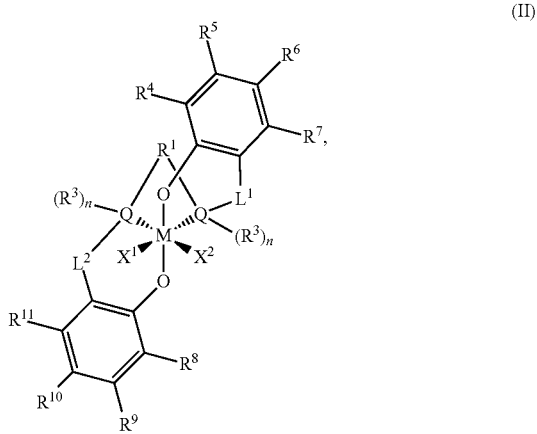

(II)

wherein:

M is a Group 4 transition metal;

each Q is independently a Group 15 atom or a Group 16 atom;

each n is independently 0 or 1, wherein n is 0 if Q is a Group 16 atom or n is 1 if Q is a Group 15 atom;

$L^1$ is

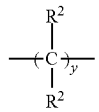

and is not part of an aromatic ring;

$L^2$ is

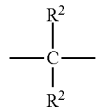

and is not part of an aromatic ring, wherein y is an integer of 2, 3, 4, 5, 6, 7, 8, 9, or 10;

each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;

$R^1$ is a substituted or unsubstituted linear, branched, cyclic, polycyclic, heterocyclic, or aromatic $C_1$-$C_{15}$ diyl;

each $R^2$ is independently a hydrogen, a halogen, a substituted or unsubstituted $C_1$-$C_{40}$ hydrocarbyl, or a heteroatom-containing group; or two or more adjacent $R^2$ groups are joined together to form a $C_4$-$C_{62}$ cyclic, polycyclic, or heterocyclic group that is not aromatic;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

2. The transition metal complex of claim 1, wherein M is Hf or Zr.

3. The transition metal complex of claim 1, wherein Q is O, N, S, or P.

4. The transition metal complex of claim 1, wherein Q is N, and wherein each $R^3$ is independently a hydrogen or a substituted or unsubstituted $C_1$-$C_{10}$ hydrocarbyl.

5. The transition metal complex of claim 1, wherein each $R^2$ is independently a hydrogen or a substituted or unsubstituted $C_1$-$C_{10}$ hydrocarbyl.

6. The transition metal complex of claim 1, wherein each $R^2$ is independently a hydrogen or a substituted or unsubstituted $C_1$-$C_5$ hydrocarbyl, and wherein y is an integer of 2, 3, 4, or 5.

7. The transition metal complex of claim 1, wherein each $R^2$ on $L^1$ and $L^2$ is independently a hydrogen or a substituted or unsubstituted $C_1$-$C_3$ hydrocarbyl, and wherein y is an integer of 2 or 3.

8. The transition metal complex of claim 1, wherein $L^1$ is an unsubstituted methanediyl and $L^2$ is an unsubstituted ethanediyl.

9. The transition metal complex of claim 1, wherein each $X^1$ and $X^2$ is independently a substituted or unsubstituted $C_1$-$C_{20}$ hydrocarbyl.

10. The transition metal complex of claim 1, wherein each $X^1$ and $X^2$ is independently a substituted or unsubstituted $C_1$-$C_8$ alkyl, a phenyl, a benzyl, a cyclohexyl, or halide-substituted analogues thereof.

11. The transition metal complex of claim 1, wherein each $X^1$ and $X^2$ is independently a halide.

12. The transition metal complex of claim 1, wherein $R^1$ is a substituted or unsubstituted linear, branched, cyclic, polycyclic, heterocyclic, or aromatic $C_1$-$C_{10}$ diyl.

13. The transition metal complex of claim 1, wherein $R^1$ is a substituted or unsubstituted linear or branched $C_1$-$C_6$ diyl.

14. The transition metal complex of claim 1, wherein $R^1$ is an unsubstituted ethanediyl.

15. The transition metal complex of claim 1, wherein each $R^4$ and $R^8$ is independently halogen, carbazolyl, fluorenyl, adamantyl, indolyl, indolinyl, imidazolyl, indenyl, indanyl, or substituted analogues thereof.

16. The transition metal complex of claim 1, wherein $R^4$ is carbazolyl, fluorenyl, adamantyl, or substituted analogues thereof, and $R^8$ is halogen.

17. The transition metal complex of claim 1, wherein each $R^5$, $R^6$, $R^7$, $R^9$, $R^{10}$, and $R^{11}$ is independently a hydrogen or a substituted or unsubstituted linear or branched $C_1$-$C_{10}$ hydrocarbyl.

18. The transition metal complex of claim 1, wherein each $R^5$, $R^7$, $R^9$, and $R^{11}$ is a hydrogen and each $R^6$ and $R^{10}$ is a substituted or unsubstituted linear or branched $C_1$-$C_4$ hydrocarbyl.

19. A catalyst system comprising an activator and the transition metal complex of claim 1.

20. The catalyst system of claim 19, wherein the catalyst system further comprises a chain transfer agent.

21. The catalyst system of claim 20, wherein the chain transfer agent comprises a $C_1$-$C_{20}$ alkyl aluminum compound, a $C_1$-$C_{20}$ alkyl zinc compound, or a combination thereof.

22. The catalyst system of claim 20, wherein the chain transfer agent comprises a $C_1$-$C_5$ alkyl aluminum compound, a $C_1$-$C_5$ alkyl zinc compound, or a combination thereof.

23. The catalyst system of claim 20, wherein the chain transfer agent is present in the catalyst system at a molar ratio of the transition metal to the chain transfer agent of 10:1 or greater.

24. The catalyst system of claim 19, wherein the activator is an alumoxane.

25. The catalyst system of claim 19, wherein the activator is a non-coordinating anion.

26. The catalyst system of claim 19, wherein the activator is selected from the group consisting of methyl alumoxane, ethyl alumoxane, isobutyl alumoxane, N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, 1-(4-(tris(pentafluorophenyl)borate)-2,3,5,6-tetrafluorophenyl)pyrrolidinium, 4-(tris(pentafluorophenyl)borate)-2,3,5,6-tetrafluoropyridine, and combinations thereof.

27. The catalyst system of claim 19, further comprising a support material.

28. A polymerization process to produce polyolefin, comprising: contacting olefin monomers with the catalyst system claim 19; and recovering olefin polymer.

29. The polymerization process of claim 28, wherein the olefin monomers comprise ethylene, propylene, or a combination thereof.

30. The polymerization process of claim 28, wherein the catalyst system or the transition metal complex has a catalytic activity in a range from about 10 kg/mmol-hr to about 1,000 kg/mmol-hr.

31. The polymerization process of claim 28, wherein the catalytic activity is in a range from about 100 kg/mmol-hr to about 1,000 kg/mmol-hr.

32. The polymerization process of claim 28, wherein the catalytic activity is in a range from about 100 kg/mmol-hr to about 600 kg/mmol-hr.

33. The polymerization process of claim 28, wherein the catalytic activity is in a range from about 200 kg/mmol-hr to about 600 kg/mmol-hr.

34. The polymerization process of claim 28, wherein the catalytic activity is in a range from about 400 kg/mmol-hr to about 600 kg/mmol-hr.

35. A transition metal complex represented by Formula (V):

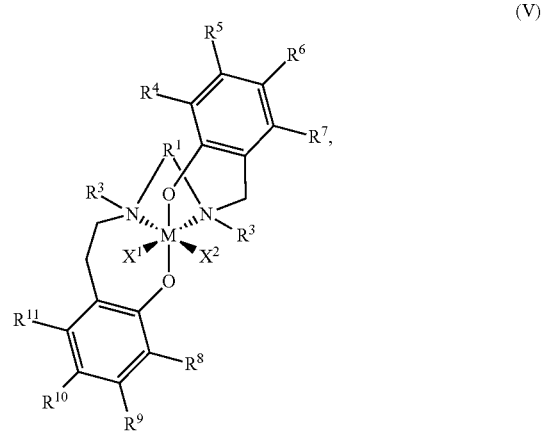

wherein:
M is a Group 4 transition metal;

each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;

$R^1$ is a substituted or unsubstituted linear, branched, cyclic, polycyclic, heterocyclic, or aromatic $C_1$-$C_{18}$ diyl;

each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, heterocyclic, or aromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

36. A transition metal complex represented by Formula (VI):

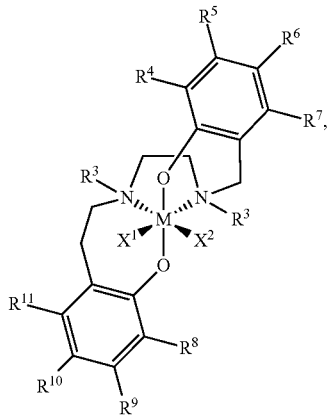

wherein:
M is Ti, Zr, or Hf,
each $X^1$ and $X^2$ is independently a substituted or unsubstituted linear, branched, cyclic, polycyclic, aromatic, or polyaromatic hydrocarbyl, a heteroatom, or a heteroatom-containing group; or $X^1$ and $X^2$ are joined together to form a $C_4$-$C_{62}$ cyclic, polycyclic, heterocyclic, or aromatic group;
each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and
each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

37. A transition metal complex represented by Formula (VII(a)):

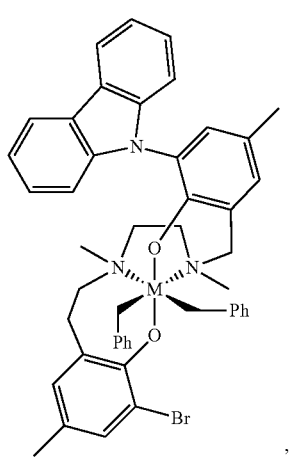

wherein M is Ti, Zr, or Hf.

38. A ligand represented by Formula (I):

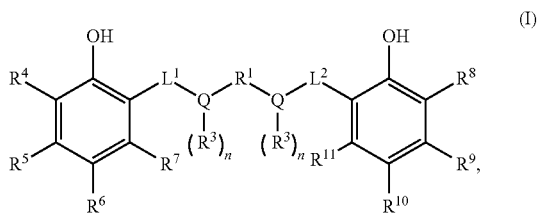

wherein:
each Q is independently a Group 15 atom or a Group 16 atom,
each n is independently 0 or 1, wherein n is 0 if Q is a Group 16 atom or n is 1 if Q is a Group 15 atom;
$L^1$ is

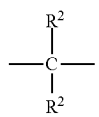

and is not part of an aromatic ring;
$L^2$ is

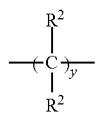

and is not part of an aromatic ring, wherein y is an integer of 2, 3, 4, 5, 6, 7, 8, 9, or 10;
$R^1$ is a substituted or unsubstituted linear, branched, cyclic, polycyclic, heterocyclic, or aromatic $C_1$-$C_{18}$ diyl;
each $R^2$ is independently a hydrogen, a halogen, a substituted or unsubstituted $C_1$-$C_{40}$ hydrocarbyl, or a heteroatom-containing group; or two or more adjacent $R^2$ groups are joined together to form a $C_4$-$C_{62}$ cyclic, polycyclic, or heterocyclic group that is not aromatic;
each $R^3$ is independently a hydrogen, a substituted or unsubstituted linear, branched, cyclic, polycyclic, aromatic, or polyaromatic $C_1$-$C_{40}$ hydrocarbyl, or a heteroatom-containing group; and
each $R^4$, $R^5$, $R^6$, $R^7$, $R^8$, $R^9$, $R^{10}$, and $R^{11}$ is independently a hydrogen, a halogen, a substituted or unsubstituted linear, branched, cyclic, polycyclic, aromatic, or polyaromatic $C_1$-$C_{40}$ hydrocarbyl, or a heteroatom-containing group; or two or more adjacent $R^4$-$R^{11}$ groups are joined together to form a $C_4$-$C_{62}$ cyclic, polycyclic, heterocyclic, or aromatic group.

39. The ligand of claim 38 wherein Q is O, N, S, or P and each $R^3$ is independently a hydrogen or a substituted or unsubstituted $C_1$-$C_{10}$ hydrocarbyl.

40. The ligand of claim 38, wherein each $R^2$ is independently a hydrogen or a substituted or unsubstituted $C_1$-$C_5$ hydrocarbyl, and wherein y is an integer of 2, 3, 4, or 5.

41. The ligand of claim 38, wherein $L^1$ is an unsubstituted methanediyl and $L^2$ is an unsubstituted ethanediyl.

42. The ligand of claim 38, wherein $R^1$ is a substituted or unsubstituted linear, branched, cyclic, polycyclic, heterocyclic, or aromatic $C_1$-$C_{10}$ diyl.

43. The ligand of claim 38, wherein each $R^4$ and $R^8$ is independently halogen, carbazolyl, fluorenyl, adamantyl, indolyl, indolinyl, imidazolyl, indenyl, indanyl, or substituted analogues thereof; and each $R^5$, $R^6$, $R^7$, $R^9$, $R^{10}$, and $R^{11}$ is independently a hydrogen or a substituted or unsubstituted linear or branched $C_1$-$C_{10}$ hydrocarbyl.

44. A ligand represented by Formula (IV(a)):

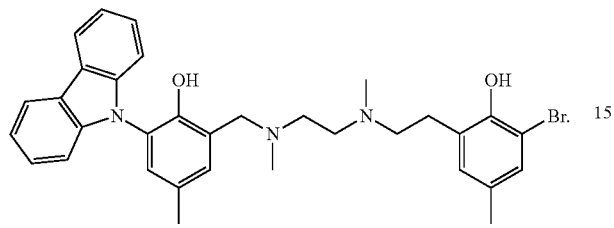
(IV(a))

* * * * *